(12) United States Patent
Noivirt-Brik et al.

(10) Patent No.: US 11,304,355 B2
(45) Date of Patent: Apr. 19, 2022

(54) METHODS AND SYSTEMS FOR REDUCING FITNESS OF WEED

(71) Applicant: Weedout Ltd., Nes Ziona (IL)

(72) Inventors: Orly Noivirt-Brik, Givataim (IL); Efrat Lidor-Nili, Nes Ziona (IL)

(73) Assignee: Weedout Ltd., Nes Ziona (IL)

( * ) Notice: Subject to any disclaimer, the term of this patent is extended or adjusted under 35 U.S.C. 154(b) by 0 days.

(21) Appl. No.: 17/053,089

(22) PCT Filed: May 6, 2019

(86) PCT No.: PCT/IB2019/053690
§ 371 (c)(1),
(2) Date: Nov. 5, 2020

(87) PCT Pub. No.: WO2019/215582
PCT Pub. Date: Nov. 14, 2019

(65) Prior Publication Data
US 2021/0068335 A1    Mar. 11, 2021

Related U.S. Application Data

(60) Provisional application No. 62/667,520, filed on May 6, 2018.

(51) Int. Cl.
*A01B 79/00* (2006.01)
*G06K 9/62* (2006.01)
(Continued)

(52) U.S. Cl.
CPC ........... *A01B 79/005* (2013.01); *A01H 1/027* (2021.01); *A01M 21/00* (2013.01); *B64C 39/024* (2013.01);
(Continued)

(58) Field of Classification Search
None
See application file for complete search history.

(56) References Cited

U.S. PATENT DOCUMENTS 8,437,498 B2 *   5/2013   Malsam ............... A01G 25/092
                                                                  382/100
2006/0053686 A1    3/2006   Halwas
(Continued)

FOREIGN PATENT DOCUMENTS

CN          102106253           6/2011
WO       WO 2014/085774         6/2014
(Continued)

OTHER PUBLICATIONS

Office Action dated Dec. 10, 2020 From the Israel Patent Office Re. Application No. 263232 and Its Translation Into English. (9 Pages).
(Continued)

*Primary Examiner* — Tahmina N Ansari

(57) ABSTRACT

A method of weed control is provided. The method comprising: (a) determining development of flowers of at least one weed species of interest; and (b) artificially pollinating at flowering the flowers of the at least one weed species of interest with pollen that reduces fitness of the at least one weed species of interest. Also provided are systems for executing the method.

19 Claims, 3 Drawing Sheets

Figure 1:
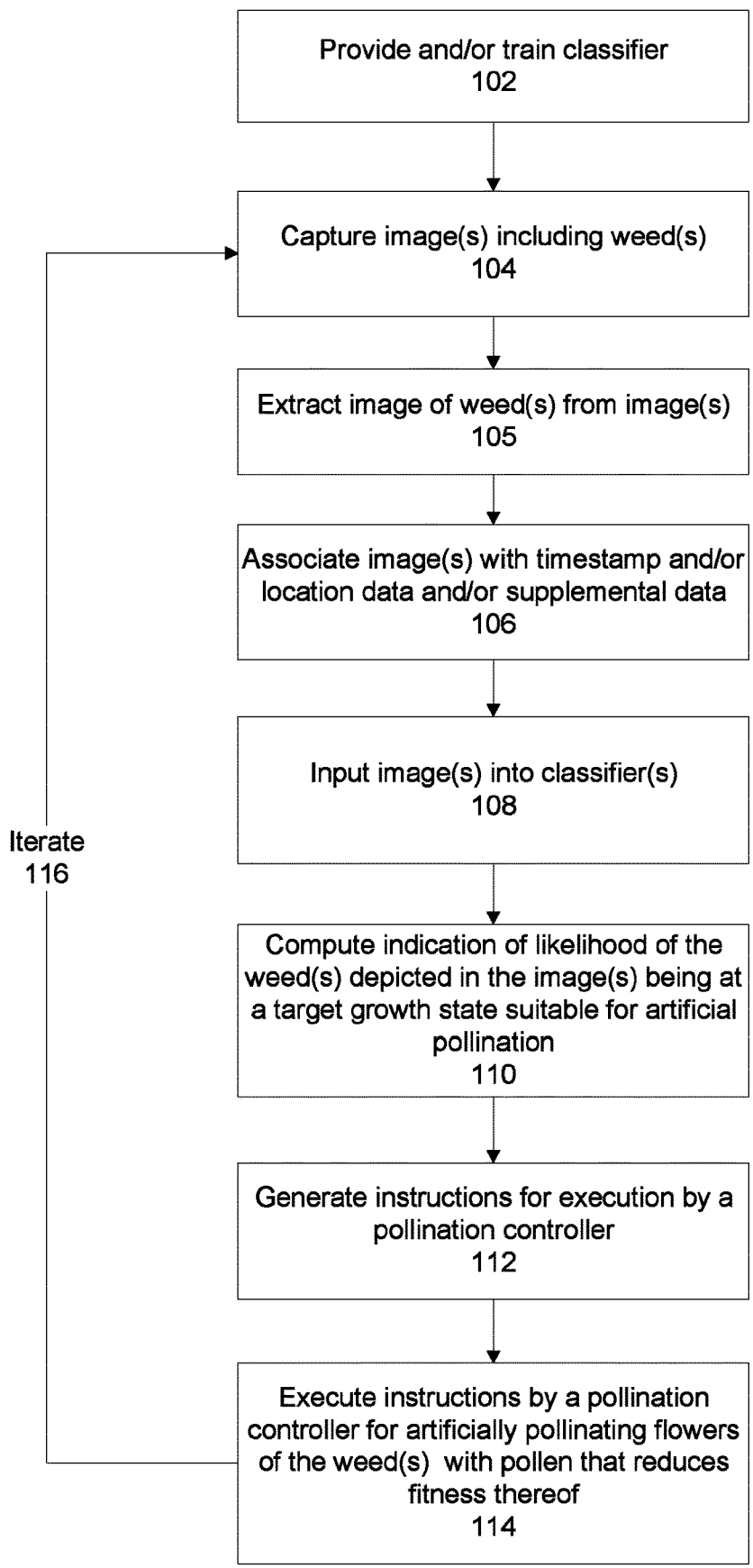

(51) Int. Cl.
| | | |
|---|---|---|
| *A01H 1/02* | (2006.01) | |
| *A01M 21/00* | (2006.01) | |
| *B64C 39/02* | (2006.01) | |
| *B64D 1/18* | (2006.01) | |
| *G06K 9/00* | (2022.01) | |

(52) U.S. Cl.
CPC ........... *B64D 1/18* (2013.01); *G06K 9/00657* (2013.01); *G06K 9/6268* (2013.01); *B64C 2201/127* (2013.01); *B64C 2201/145* (2013.01)

(56) References Cited

U.S. PATENT DOCUMENTS

| | | | |
|---|---|---|---|
| 2017/0042102 A1 | 2/2017 | Safreno | |
| 2017/0359943 A1 | 12/2017 | Calleija et al. | |
| 2018/0065749 A1 | 3/2018 | Cantrell | |
| 2019/0208790 A1* | 7/2019 | Lidor-Nili | C12N 15/8287 |
| 2020/0275617 A1* | 9/2020 | Fabijanski | C05F 3/00 |
| 2020/0281139 A1 | 9/2020 | Noivirt-Brik et al. | |
| 2020/0288656 A1 | 9/2020 | Lidor-Nili et al. | |
| 2020/0288657 A1 | 9/2020 | Novirt-Brik et al. | |
| 2021/0127610 A1 | 5/2021 | Lidor-Nili et al. | |

FOREIGN PATENT DOCUMENTS

| | | | |
|---|---|---|---|
| WO | WO 2016/191825 | 12/2016 | |
| WO | WO 2017/194399 | 11/2017 | |
| WO | WO 2017/203519 | 11/2017 | |
| WO | WO-2017194399 A1 * | 11/2017 | ......... G06K 9/00671 |
| WO | WO 2007/093444 | 7/2018 | |
| WO | WO 2019/106666 | 6/2019 | |
| WO | WO 2019/106667 | 6/2019 | |
| WO | WO 2019/106668 | 6/2019 | |
| WO | WO 2019/215581 | 11/2019 | |
| WO | WO 2019/215582 | 11/2019 | |
| WO | WO 2020/084586 | 4/2020 | |
| WO | WO 2020/084586 A9 | 10/2020 | |

OTHER PUBLICATIONS

Official Action dated Dec. 30, 2020 from the US Patent and Trademark Office Re. U.S. Appl. No. 16/304,145. (37 pages).
Bae et al. "Production of Unbolting Lines Through Gamma-Ray Irradiation Mutagenesis in Genetically Modified Herbicide-Tolerant Zoysia Japonica", Breeding Science, 59(1): 103-105, 2009.
Official Action dated Feb. 2, 2021 From the US Patent and Trademark Office Re. U.S. Appl. No. 16/884,097. (36 Pages).
Culpepper et al. "Glyphosate-Resistant Palmer Amaranth (*Amaranthus palmeri*) Confirmed in Georgia", Weed Science, 54(4):620-626, Jul. 1, 2006.
Daher et al. "Optimization of Conditions for Germination of Cold-Stored *Arabidopsis thaliana* Pollen", Plant Cell Reports, 28: 347-357, 2009.
Preston et al. "A Decade of Glyphosate-Resistant Lolium around the World: Mechanisms, Genes, Fitness, and Agronomic Management", Weed Science, 57(4):435-441, Jul. 1, 2009.
Tacconi et al. "Kiwifruit Pollination: the Interaction Between Pollen Quality, Pollination Systems and Flowering Stage", Journal of Berry Research, 6(4): 417-426, Dec. 12, 2016.
Communication Pursuant to Article 94(3) EPC dated Nov. 20, 2020 From the European Patent Office Re. Application No. 17802323.0. (5 Pages).
International Preliminary Report on Patentability dated Nov. 19, 2020 From the International Bureau of WIPO Re. Application No. PCT/IB2019/053688. (7 Pages).
International Preliminary Report on Patentability dated May 6, 2021 From the International Bureau of WIPO Re. Application No. PCT/IB2019/059171. (7 Pages).
International Preliminary Report on Patentability dated Dec. 6, 2018 From the International Bureau of WIPO Re. Application No. PCT/IL2017/050568. (8 Pages).
International Preliminary Report on Patentability dated Jun. 11, 2020 From the International Bureau of WIPO Re. Application No. PCT/IL2018/051301. (8 Pages).
International Preliminary Report on Patentability dated Jun. 11, 2020 From the International Bureau of WIPO Re. Application No. PCT/IL2018/051302. (7 Pages).
International Preliminary Report on Patentability dated Jun. 11, 2020 From the International Bureau of WIPO Re. Application No. PCT/IL2018/051303. (8 Pages).
International Search Report and the Written Opinion dated Dec. 12, 2019 From the International Searching Authority Re. Application No. PCT/IB2019/059171. (9 Pages).
International Search Report and the Written Opinion dated Aug. 14, 2019 From the International Searching Authority Re. Application No. PCT/IB2019/053690. (13 Pages).
International Search Report and the Written Opinion dated Jul. 14, 2019 From the International Searching Authority Re. Application No. PCT/IB2019/053688. (10 Pages).
International Search Report and the Written Opinion dated Feb. 21, 2019 From the International Searching Authority Re. Application No. PCT/IL2018/051301. (11 Pages).
International Search Report and the Written Opinion dated Aug. 23, 2017 From the International Searching Authority Re. Application No. PCT/IL2017/050568. (11 Pages).
International Search Report and the Written Opinion dated Feb. 24, 2019 From the International Searching Authority Re. Application No. PCT/IL2018/051302. (9 Pages).
International Search Report and the Written Opinion dated Feb. 26, 2019 From the International Searching Authority Re. Application No. PCT/IL2018/051303. (11 Pages).
Office Action dated Jul. 9, 2019 From the Israel Patent Office Re. Application No. 263232 and Its Translation Into English. (5 Pages).
Restriction Official Action dated Oct. 1, 2020 from the US Patent and Trademark Office Re. U.S. Appl. No. 16/304,145. (9 pages).
Supplementary European Search Report and the European Search Opinion dated Oct. 25, 2019 From the European Patent Office Re. Application No. 17802323.0. (9 Pages).
Al-Ahmad et al. "Mitigation of Establishment of *Brassica napus* Transgenes in Volunteers Using A Tandem Construct Containing A Selectively Unfit Gene", Plant Biotechnology Journal, XP055444715, 4(1): Jan. 7-21, 2006. Abstract, p. 16, r-h col. 1st Para, p. 17, 1-h col., 4th Para.
Al-Ahmad et al. "Mitigation Using A Tandem Construct Containing A Selectively Unfit Gene Precludes Establishment of *Brassica napus* Transgenes in Hybrids and Backcrosses With Weedy *Brassica rapa*", Plant Biotechnology Journal, XP055444720, 4(1): 23-33, Published Online Aug. 16, 2005. Abstract, Table S2, p. 31, 1-h col., Lines 10-11, 18-23.
Chin et al. "Pollination With Irradiated Pollen in Rice—*Oryza sativa* L. I. First (M1) Generation", Heredity, 63(2): 163-170, Published Online Oct. 1, 1989.
Germana "Use of Irradiated Pollen to Induce Parthenogenesis and Haploid Production in Fruit Crops", Plant Mutation Breeding and Biotechnology, XP009516584, p. 411-415, Published Online Dec. 31, 2012.
Gressel et al. "A Strategy to Provide Long-Term Control of Weedy Rice While Mitigating Herbicide Resistance Transgene Flow, and Its Potential Use for Other Crops With Related Weeds", Pest Management Science, XP055053395, 65(7): 723-731, Published Online Apr. 14, 2009.
Jordan et al. "Biorational Management Tactics to Select Against Triazine-Resistant Amaranthus Hybridus: A Field Trial", Journal of Applied Ecology, 36(1): 123-132, Feb. 1999.
Keller et al. "Genetic Introgression From Distant Provenances Reduces Fitness in Local Weed Populations", Journal of Applied Ecology, 37(4): 647-659, Aug. 2000.
Kurtar "Influence of Gamma Irradiation on Pollen Viability, Germination Ability, and Fruit and Seed-Set of Pumpkin and Winter Squash", African Journal of Biotechnology, 8(24): 6918-6926, Dec. 15, 2009.
Kwit et al. "Transgene Introgression in Crop Relatives: Molecular Evidence and Mitigation Strategies", Trends in Biotechnology, XP002794936, 29(6): 284-293, Published Online Mar. 8, 2011.

(56) References Cited

OTHER PUBLICATIONS

Lagera et al. "Varying Sugars and Sugar Concentrations Influence In Vitro Pollen Germination and Pollen Tube Growth of *Cassia alata* L.", Journal of Young Investigations, 33(1): 42-45, Jun. 2017.
Li et al. "Effects of Sowing Date on Phenotypic Plasticity of Fitness-Related Traits in Two Annual Weeds on the Songnen Plain of China", PLOS One, 10(5): e0127795-1-0127795-15, May 29, 2005.
Ma "Why Don't They Genetically Modify Weeds Instead of Crops? Wouldn't It Make More Sense to Genetically Alter Species of Weeds to Become Interfile After A Few Generations, Thereby Reducing the Need for Herbicides?", Quora.com, 1 P., Apr. 2, 2014.
Munusamy et al. "Female Reproductive System of Amaranthus as the Tarset for Agrobacterium-Mediated Transformation", Advances in Biscience and Biotechnology, 4(2): 188-192, Published Online Feb. 28, 2013.
Peixe et al. "Gamma-Irradiated Pollen Induces the Formation of 2n Endosperm and Abnormal Embryo Development in European Plum (*Prunus domestica* L., Cv. 'Rainha Claudia Verde')", Scientia Horticulturae, 86(4): 267-278, Dec. 2000.
Shu "Use of Irradiated Pollen to Induce Pathogenesis and Haploid Production in Fruit Crops", Plant Mutation Breeding and Biotechnology, C30: 412-416, Dec. 2012.
Yang et al. "Molecular Genetic Analysis of Poffen Irradiation Mutagenesis in *Arabidopsis*", New Phytologist, XP055615348, 164(2): 279-288, Published Online Sep. 10, 2004.
Notification of Office Action dated Jul. 2, 2021 From the State Intellectual Property Office of the People's Republic of China Re. Application No. 201780037868.0 and Its English Summary. (6 Pages).
Translation Dated Jul. 14, 2021 of Notification of Office Action dated Jul. 2, 2021 From the State Intellectual Property Office of the People's Republic of China Re. Application No. 200880024068. (6 Pages).
Translation Dated Jul. 14, 2021 of Notification of Office Action dated Jul. 2, 2021 From the State Intellectual Property Office of the People's Republic of China Re. Application No. 201780037868.0. (6 Pages).
He "Garden Plant Breeding", China Forestry Publishing House: 174-189, Aug. 1992. Chinese Document only).
Communication Pursuant to Article 94(3) EPC dated Aug. 12, 2021 From the European Patent Office Re. Application No. 17802323.0. (7 Pages).
Examination Report Under Sections 12 & 13 of the Patents Act, 1970 and the Patents Rules, 2003 dated Jul. 16, 2021 From the Government of India. Intellectual Property India, Patents, Designs, Trade Marks, Geographical Indications, The Patent Office Re. Application No. 201827046713. (7 Pages).
Final Official Action dated Sep. 16, 2021 from the US Patent and Trademark Office Re. U.S. Appl. No. 16/304,145. (32 pages).
Restriction Official Action dated Aug. 2, 2021 from the US Patent and Trademark Office Re. U.S. Appl. No. 16/885,311. (8 pages).
Restriction Official Action dated Jul. 12, 2021 from the US Patent and Trademark Office Re. U.S. Appl. No. 16/884,362. (8 pages).
Supplementary European Search Report and the European Search Opinion dated Aug. 13, 2021 From the European Patent Office Re. Application No. 18883157.2, (120 Pages).
Supplementary European Search Report and the European Search Opinion dated Aug. 13, 2021 From the European Patent Office Re. Application No. 18883823.9. (8 Pages).

\* cited by examiner

METHODS AND SYSTEMS FOR REDUCING FITNESS OF WEED

RELATED APPLICATION/S SECTION

This application is a National Phase of PCT Patent Application No. PCT/IB2019/053690 having International filing date of May 6, 2019, which claims the benefit of priority under 35 USC § 119(e) of U.S. Provisional Patent Application No. 62/667,520 filed on May 6, 2018. The contents of the above applications are all incorporated by reference as if fully set forth herein in their entirety.

FIELD AND BACKGROUND OF THE INVENTION

The present invention, in some embodiments thereof, relates to methods and systems for weed control.

Weeds have been the major biotic cause of crop yield loses since the origins of agriculture. The potential of weed damages is estimated as 34% loss of crop yield, on average, world-wide [Oerke, E-C., 2006]. In the USA alone, the annual cost of crop losses due to weeds is greater than 26 billion USD [Pimentel D et al., 2000]. Furthermore according to the Weed Science Society of America Weeds are estimated to cause more than 40 billion USD in annual global losses [wssa(dot)net/wssa/weed/biological-control/]. Weeds are thus a major threat to food security [Delye et al., 2013].

Herbicides are the most commonly used and effective weed control tools. Due to the intense selection pressure exerted by herbicides, herbicide resistance is constantly growing and as of 2016 there are over 470 weed biotypes currently identified as being herbicide resistant to one or more herbicides by The International Survey of Herbicide Resistant Weeds (weedscience(dot)org/).

Weeds, like other plants, have several sexual reproduction mechanisms: self-pollination, cross-pollination, or both. Self-pollination describes pollination using pollen from one flower that is transferred to the same or another flower of the same plant. Cross-pollination describes pollination using pollen delivered from a flower of a different plant. Weeds rely on wind, or animals such as bees and other insects to pollinate them.

Since the 1940's the use of sterile organisms has been reported for use in order to reduce pest population and the success of these methods was demonstrated in many cases such as the tsetse fly [Klassen& Curtis, 2005], melon fly [Yosiaki et al. 2003] and Sweet potato weevil [Kohama et al., 2003].

Planting in the field plants producing sterile pollen for the production of infertile seeds was mentioned but immediately over-ruled due to practical, regulatory and economic reasons. (quora(dot)com/Why-dont-they-genetically-modify-weeds-instead-of-crops).

PCT Publication No. WO2017/203519 discloses a method of weed control comprising artificially pollinating a weed species of interest with pollen of the same species that reduces fitness of the weed species of interest, thereby blocking the next generation of viable weed seeds.

PCT Publication No. WO2007093444 discloses a method for determining the point at which a plant starts to flower.

US20180065749 discloses a method and a system for pollinating crops via unmanned vehicles.

SUMMARY OF THE INVENTION

According to an aspect of some embodiments of the present invention there is provided a method of weed control, the method comprising:

(a) determining development of flowers of at least one weed species of interest; and (b) artificially pollinating at flowering the flowers of the at least one weed species of interest with pollen that reduces fitness of the at least one weed species of interest.

According to some embodiments of the invention, the pollinating the flowers is at stigma receptive stage.

According to some embodiments of the invention, the pollinating the flowers is at anthesis.

According to some embodiments of the invention, the determining development of flowers comprises determining pre-flowering.

According to some embodiments of the invention, the determining development of flowers comprises determining development of inflorescence meristem.

According to some embodiments of the invention, the determining development of flowers comprises determining anthesis.

According to some embodiments of the invention, the determining development of flowers comprises identification of female structures.

According to some embodiments of the invention, the determining development of flowers comprises identification of male structures.

According to some embodiments of the invention, the determining comprises visual determination.

According to some embodiments of the invention, the determining comprises digital imaging.

According to some embodiments of the invention, the determining comprises spectral determination.

According to some embodiments of the invention, the spectral determination comprises multispectral determination or hyperspectral determination.

According to some embodiments of the invention, the determining comprises molecular determination.

According to some embodiments of the invention, the determining comprises chemical determination.

According to some embodiments of the invention, the determining comprises determining an amount of air pollen.

According to some embodiments of the invention, the determining is per plant.

According to some embodiments of the invention, the determining is effected on a plurality of plants in a growth area.

According to some embodiments of the invention, the determining comprises integrating plant data and/or field data with literature data.

According to some embodiments of the invention, the step (a) and/or step (b) are effected more than once.

According to some embodiments of the invention, the growth area comprises a crop.

According to some embodiments of the invention, the determining and/or pollinating is performed without affecting the crop.

According to some embodiments of the invention, the pollinating is effected prior to and/or post harvesting of the crop and/or at late season.

According to some embodiments of the invention, the determining and/or pollinating is effected using a ground machinery.

According to some embodiments of the invention, the ground machinery is adapted to crop height and optionally comprises a height control system for the pollinating.

According to some embodiments of the invention, the ground machinery comprises a static puffer.

According to some embodiments of the invention, the determining and/or pollinating is effected using an aerial machinery.

According to some embodiments of the invention, the aerial machinery is selected from the group consisting of an unmanned aerial vehicle (UAV), remote piloted vehicle (RPV), drone, a pollinating insect, pollinating bee, a robot and a robotic bee.

According to some embodiments of the invention, the pollinating is effected using insects.

According to some embodiments of the invention, the determining and/or pollinating is effected using a precision agricultural tool.

According to some embodiments of the invention, the pollinating is effected using a wet spray formulation.

According to some embodiments of the invention, the pollinating is effected using a dry spray formulation.

According to some embodiments of the invention, the pollinating is only of female flowers.

According to some embodiments of the invention, the determining and pollinating are effected concomitantly.

According to some embodiments of the invention, the method further comprises identifying the at least one weed species.

According to some embodiments of the invention, the identifying comprises the use of light reflectance, visual identification and/or imaging.

According to some embodiments of the invention, the at least one weed species of interest and the pollen are of the same weed species.

According to some embodiments of the invention, the at least one weed species of interest and the pollen are of different weed species.

According to some embodiments of the invention, the artificially pollinating is effected in a large scale setting.

According to some embodiments of the invention, the weed species of interest is a herbicide resistant weed.

According to some embodiments of the invention, the method further comprises treating the at least one weed species of interest with a herbicide.

According to some embodiments of the invention, the treating is prior to the pollinating.

According to some embodiments of the invention, the pollen is coated with the herbicide. According to some embodiments of the invention, the pollen reduces productiveness of the weed species of interest.

According to some embodiments of the invention, reduction in the productiveness is manifested by:
(i) inability to develop an embryo;
(ii) embryo abortion;
(iii) seed non-viability;
(iv) seed that cannot fully develop; and/or
(v) seed that is unable to germinate.

According to some embodiments of the invention, the pollen is non-genetically modified pollen.

According to some embodiments of the invention, the non-genetically modified pollen is irradiated pollen.

47. The method of any one of claims 1-44, wherein the pollen is genetically modified pollen.

According to some embodiments of the invention, the weed species of interest is an annual weed.

According to some embodiments of the invention, the weed species of interest is a perennial weed.

According to some embodiments of the invention, the weed species of interest is a biennial weed.

According to some embodiments of the invention, the weed species of interest or the pollen is of the *Amaranthus* genus.

According to an aspect of some embodiments of the present invention there is provided a system for reducing fitness of at least one weed species of interest, comprising:

a non-transitory memory having stored thereon a code for execution by at least one hardware processor, the code comprising:

code for inputting into at least one classifier, at least one image captured by at least one imaging sensor, the at least one image depicting at least one weed species of interest;

code for computing by the at least one classifier, an indication of likelihood of the at least one weed being at a state suitable for artificial pollination of flowers of the at least one weed species of interest at a certain time interval, wherein the at least one classifier is trained on a training dataset comprising a plurality of images of respective at least one weed species of interest captured by the at least one imaging sensor and associated indication of a time interval of when the respective at least one weed species of interest is at the target growth state suitable for artificial pollination of flowers thereof relative to the time of capture of the respective image; and code for generating according to the indication of likelihood and the certain time interval, instructions for execution by pollination controller of a pollinator device for artificially pollinating flowers of the at least one weed species of interest with pollen that reduces fitness of the at least one weed species of interest.

According to some embodiments of the invention, the target growth state suitable for artificial pollination of flowers of the at least one weed species of interest comprises flowering of the at least one weed species of interest.

According to some embodiments of the invention, the certain time interval is a future time interval relative to the time at which the at least one image is captured.

According to some embodiments of the invention, the certain time interval denotes a current time.

According to some embodiments of the invention, the at least one image captured by at least one imaging sensor depicts the at least one weed species of interest at a growth stage prior the start of flowering.

According to some embodiments of the invention, the system further comprises a code for execution of the generated instructions for artificially pollinating flowers of the at least one weed species of interest with pollen that reduces fitness of the at least one weed species of interest.

According to some embodiments of the invention, the instructions for execution by pollination controller are computed by at least one classifier according to the training dataset that further includes, in association with each of the plurality of images, respective instructions for execution by pollination controller of a pollinator device for artificially pollinating flowers of the at least one weed species of interest with pollen that reduces fitness of the at least one weed species of interest.

According to some embodiments of the invention, the at least one image sensor is coupled to a first machinery navigating over the field, and the instructions for execution comprise code instruction for automated execution by the pollination controller of the pollinator device coupled to a second machinery navigating over the field, wherein the at least one image is iteratively acquired by the at least one sensor and the pollination controller of the pollinator device iteratively executes the code instructions as the first machinery and the second machinery navigate over the field for real-time pollination of identified at least one weed species of interest.

According to some embodiments of the invention, the first machinery and the second machinery are selected from the following types of machinery: ground based machinery and aerial based machinery.

According to some embodiments of the invention, the first machinery and the second machinery are implemented as the same type of machinery, or the first machinery and the second machinery are implemented as different types of machinery.

According to some embodiments of the invention, the pollinator device comprises precision agricultural tools.

According to some embodiments of the invention, the at least one image sensor is captured during a first time interval, and the instructions for execution comprise code instruction for automated execution by the pollination controller of the pollinator are executed at a second time interval spaced apart in time after the first time interval, wherein the second time interval is according to the certain time interval computed by the classifier.

According to some embodiments of the invention, the at least one image sensor is coupled to a first machinery navigating over the field during the first time interval, and the pollination controller is coupled to a second machinery navigating over the field during the second time interval.

According to some embodiments of the invention, the at least one classifier further computes for the at least one image, a classification indication of at least one of a female of the at least one weed species of interest or a male of the at least one weed species of interest, wherein the instructions for artificially pollinating flowers are generating according to the classification indication, and wherein images of the training set respectively include a classification indication of a female of the at least one weed species of interest.

According to some embodiments of the invention, the at least one image is further associated with a tag storing a geographical location indication of the at least one weed species of interest captured within the at least one image, the geographic location outputted by at least one geographic positioning sensor, and wherein the instructions for pollination of the at least one weed species of interest are generated according to the geographic location of the at least one weed.

According to some embodiments of the invention, the instructions for pollination are created according to a plurality of images, each image associated with a different geographical location, the instructions for pollination comprise sub-sets of instructions for administering pollen to each at least one weed species of interest located at respective geographical locations of a field.

According to some embodiments of the invention, each of the sub-sets of instructions is selected for execution by the pollination controller of the pollinator device according to a real-time geographic location of a machinery navigating over the field.

According to some embodiments of the invention, the instructions are generated in real time according to a real time location of the pollination device outputted by a geographical location sensor that senses the location of the pollination device.

According to some embodiments of the invention, the instructions are generated in real time according to at least one environmental condition parameter outputted by at least one environmental condition sensor that senses the environmental condition in proximity to the at least one weed species of interest, wherein the instructions are generate according to a predicted dispersion pattern of the applied pollen according to the at least one environmental condition parameter.

According to some embodiments of the invention, the at least one imaging sensor is selected from the group consisting of: a reflectance sensor that captures light applied by a light source reflected from the at least one weed species of interest, a spectral image sensor, multispectral image sensor, hyperspectral image sensor, and a visible light sensor.

According to some embodiments of the invention, the pollinator device comprises a sprayer located at a predefined height above the ground, and above crops growing in the field where the at least one weed species of interest is growing.

According to some embodiments of the invention, the pollinator device is coupled to an aerial based machinery selected from the group consisting of: an unmanned aerial vehicle (UAV), a remote-piloted vehicle (RPV), a drone, a specialized robot, a robot bee, a robobee, and a robo-bee.

According to some embodiments of the invention, the pollinator device comprises a mechanism to attract bees, and couple the pollen to the bees for administration to the flower of the at least one weed species of interest.

According to some embodiments of the invention, the instructions are generated according to a supplemental data profile including multiple supplemental data parameters indicative of the environment of the weed and/or details of the pollination to be applied and/or hardware of the pollinator device.

According to an aspect of some embodiments of the present invention there is provided a system for training at least one classifier for reducing fitness of at least one weed species of interest, comprising:

a non-transitory memory having stored thereon a code for execution by at least one hardware processor, the code comprising:

code for accessing a training dataset comprising a plurality of images of respective at least one weed species of interest captured by at least one imaging sensor and associated indication of a time interval of when the respective at least one weed species of interest is at a target growth state suitable for artificial pollination of flowers thereof relative to the time of capture of the respective image; and code for training at least one classifier according to the training dataset, for computing an indicative of likelihood of a target at least one weed being at a target growth state suitable for artificial pollination of flowers of the at least one weed species of interest at a certain time interval according to at least one target image captured by at least one imaging sensor.

According to an aspect of some embodiments of the present invention there is provided a method of reducing fitness of at least one weed species of interest, comprising:

inputting into at least one classifier, at least one image captured by at least one imaging sensor, the at least one image depicting at least one weed species of interest;

computing by the at least one classifier, an indication of likelihood of the at least one weed being at a target growth state suitable for artificial pollination of flowers of the at least one weed species of interest at a certain time interval, wherein the at least one classifier is trained on a training dataset comprising a plurality of images of respective at least one weed species of interest captured by the at least one imaging sensor and associated indication of a time interval of when the respective at least one weed species of interest is at the target growth state suitable for artificial pollination of flowers thereof relative to the time of capture of the respective image; and generating according to the indication of likelihood and the certain time interval, instructions for execution by pollination controller of a pollinator device for artificially pollinating flowers of the at least one weed species of interest with pollen that reduces fitness of the at least one weed species of interest.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 2:
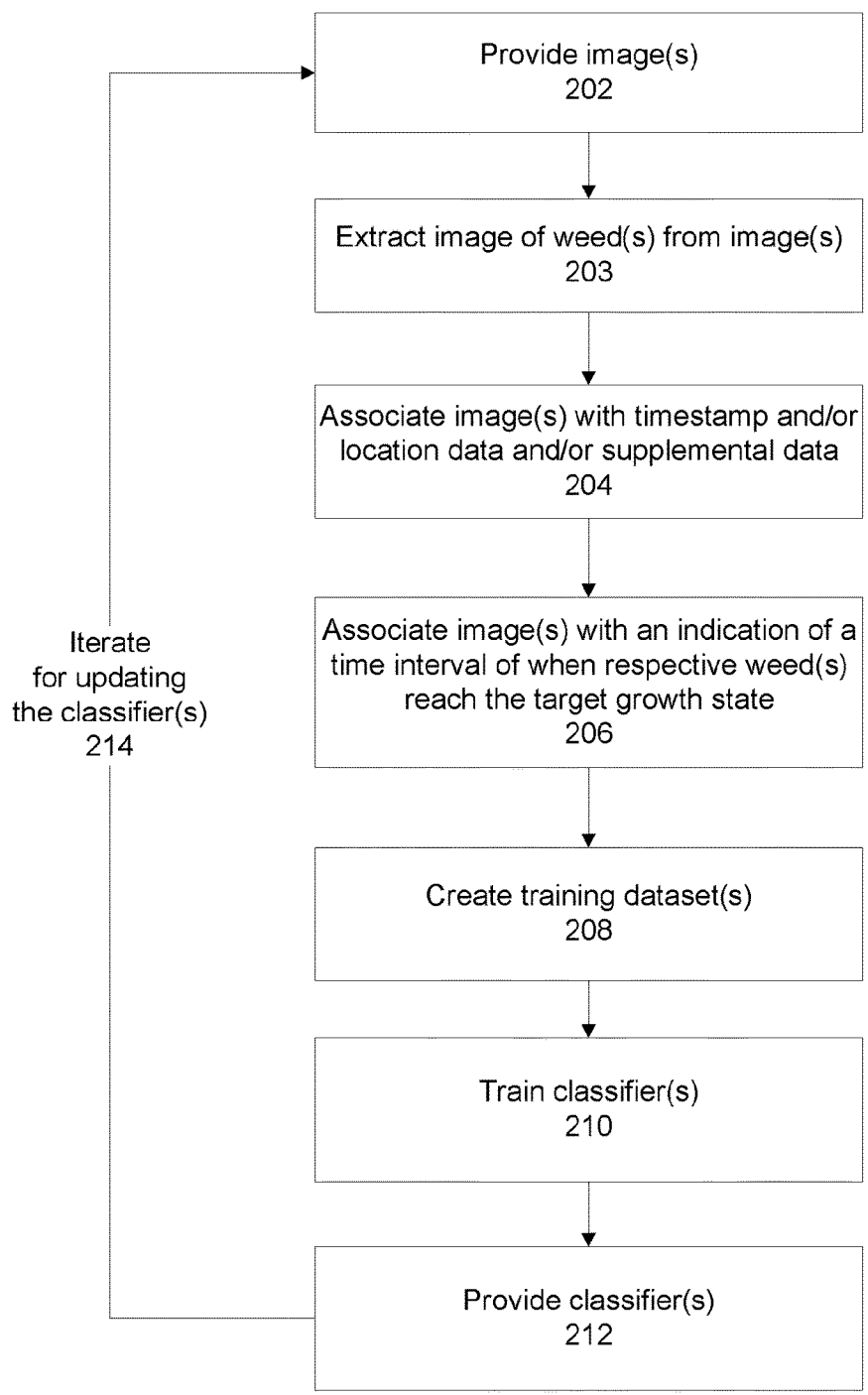
Figure 3:
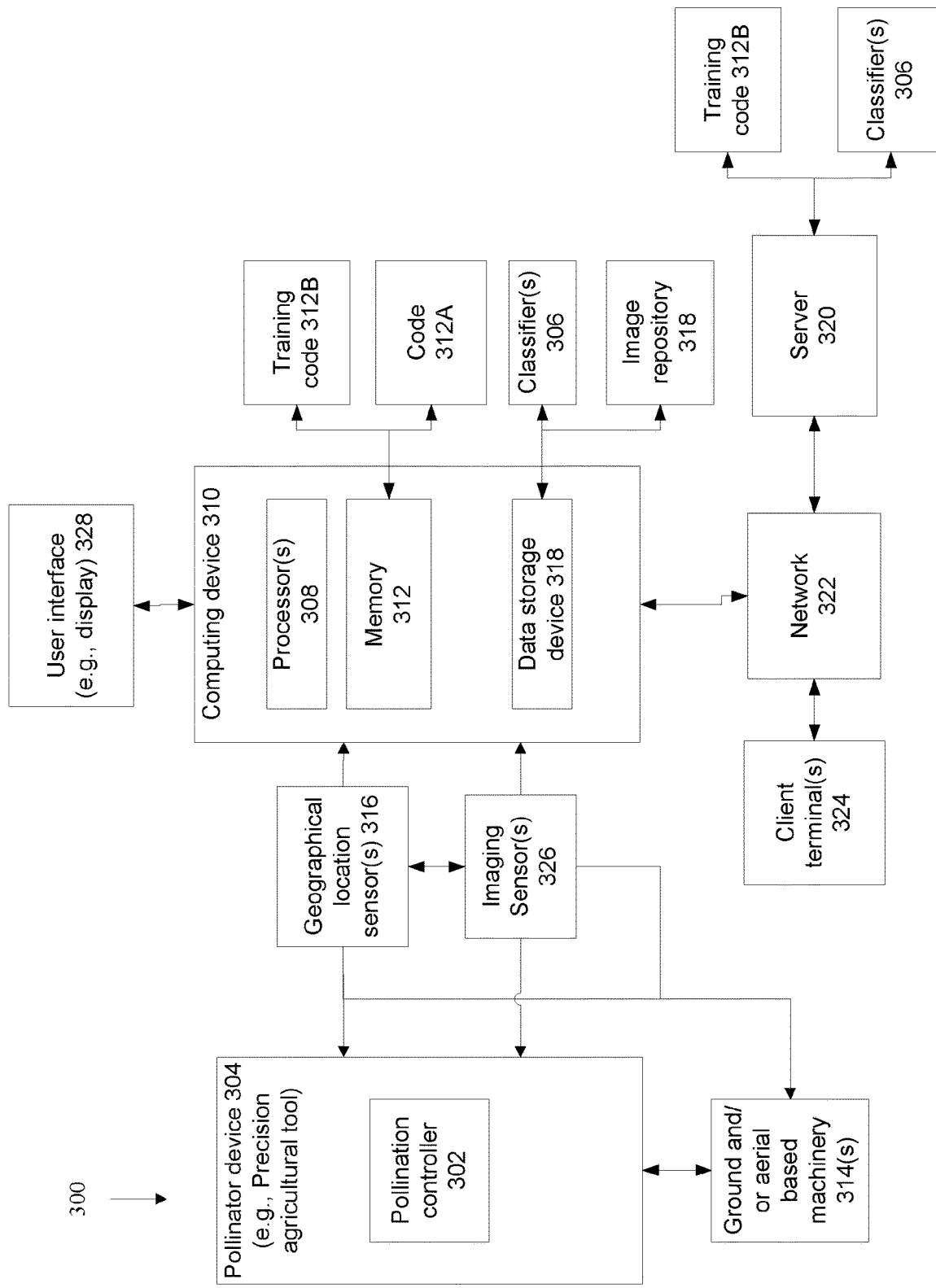

In the drawings:

FIG. 1 is a flowchart of a method for reducing fitness of at least one weed species of interest, in accordance with some embodiments of the present invention;

FIG. 2 is a flowchart of a method of training one or more statistical classifiers for reducing fitness of at least one weed species of interest, in accordance with some embodiments of the present invention; and FIG. 3 is a block diagram of components of a system for providing a pollination controller of a pollinating device with instructions for artificially pollinating flowers of the at least one weed species of interest with pollen that reduces fitness of the at least one weed species of interest, and/or for training one or more statistical classifiers for reducing fertilization of weeds in a field, in accordance with some embodiments of the present invention.

DESCRIPTION OF SPECIFIC EMBODIMENTS OF THE INVENTION

The present invention, in some embodiments thereof, relates to methods and systems for weed control.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to an aspect there is provided a method of weed control, the method comprising:

(a) determining development of flowers of at least one weed species of interest; and (b) artificially pollinating at flowering said flowers of said at least one weed species of interest with pollen that reduces fitness of said at least one weed species of interest.

As used herein the term "weed species of interest" refers to a wild plant growing where it is not wanted and that may be in competition with cultivated plants of interest (i.e., crop-desirable plants). Weeds are typically characterized by rapid growth and/or ease of germination, and/or competition with crops for space, light, water and nutrients. According to some embodiments of the invention, the weed species of interest is traditionally non-cultivated.

According to another embodiment of the invention, the weed is a perennial weed.

According to another embodiment of the invention the weed is a biennial weed.

According to another embodiment of the invention the weed is an annual weed.

According to another embodiment of the invention the weed is a therophyte.

According to an embodiment, the weed is a parasitic plant.

Examples of weed species which can be targeted (mitigated) according to the present teachings include, but are not limited to,

*Amaranthus* species—*A. albus, A. blitoides, A. hybridus, A. palmeri, A. powellii, A. retroflexus, A. rudis, A. spinosus, A. tuberculatus, A. thunbergii, A. graecizans* and *A. viridis; Ambrosia* species—*A. trifida, A. artemisifolia; Lolium* species—*L. multiflorum, L. rigidium, L perenne; Digitaria* species—*D. insularis, D. sanguinalis; Euphorbia* species—*E. heterophylla; Kochia* species—*K. scoparia; Sorghum* species—*S. halepense; Conyza* species—*C. bonariensis, C. canadensis, C. sumatrensis; Chloris* species—*C. truncate; Echinochola* species—*E. colona, E. crus-galli; Eleusine* species—*E. indica; Poa* species—*P. annua; Plantago* species—*P. lanceolata; Avena* species—*A. fatua; Chenopodium* species—*C. album; Setaria* species—*S. viridis, Abutilon theophrasti, Ipomoea* species, *Sesbania*, species, *Xanthium strumarium, Cassia* species, *Sida* species, *Brachiaria* species, *Sporobolus* species—*S. pyramidalis, S. natalensis, S. jacquemontii, S. fertilis, S. africanus S. indicus, Solanum nigrum, Solanum carolinense,* and *Solanum elaeagnifolium.*

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridisvar, robusta-alba schreiber, Setaria viridisvar, robusta-purpurea, Snowdenia polystachea, Sorghum Sudanese, Alisma plantago-aquatica, Amaranthus lividus, Ammaniaauriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandravar, pedicellata, Euphorbia heterophylla, Fallopia convolvulus, Fimbristylis miliacea, Galeopsis tetrahit, Galium spurium, Helianthus annuus, Iva xanthifolia, Ixophorusunisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubiavar,* major, *Lindernia micrantha, Lindernia procumbens, Mesembryanthemum crystallinum, Monochoria kor-*

*sakowii, Monochoria vaginalis, Neslia paniculata, Papaver rhoeas, Parthenium hysterophorus, Pentzia suj fruticosa, Phalaris minor, Raphanus raphanistrum, Raphanus sativus, Rapistrum rugosum, Rotalaindicavar, uliginosa, Sagittaria guyanensis, Sagittaria montevidensis, Sagittaria pygmaea, Salsola iberica, Scirpus juncoidesvar, ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucuscarota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea, and Senecio vulgaris.*

According to a specific embodiment the weed species is selected from or belong to the group consisting of *Amaranthus: A. palmeri, A. tuberculatus, Lolium rigidum, Lolium multiflorum, Lolium perenne Ambrosia: A. trifida, A. artemisiifolia, Kochia scoparia, Conyza: C. canadensis, C. bonariensis, Echinochloa, Alopecurus myosuroides, Sorghum halepense, Digitaria insularis, Eleusine indica, Avena fatua, Euphorbia Heterophylla* and *Chenopodium album.*

According to an embodiment, the weed is a parasitic plant. Examples of parasitic plants include, but are not limited to, *Striga* sp, *Orobanche* sp, *Cuscuta* sp, Mistletoe.

Different weed may have different growth habits and therefore specific weeds usually characterize a certain crop in given growth conditions.

According to a specific embodiment, the weed is a herbicide resistant weed.

According to a specific embodiment, weed is defined as herbicide resistant when it meets the Weed Science Society of America (WSSA) definition of resistance.

Accordingly, WSSA defines herbicide resistance as "the inherited ability of a plant to survive and reproduce following exposure to a dose of herbicide normally lethal to the wild type. Alternatively, herbicide resistance is defined as "The evolved capacity of a previously herbicide-susceptible weed population to withstand an herbicide and complete its life cycle when the herbicide is used at its normal rate in an agricultural situation" (Source: Heap and Lebaron. 2001 in Herbicide Resistance and World Grains).

As used herein the phrase "weed control" refers to suppressing growth and optionally spread of a population of at least one weed species of interest and even reducing the size of the population in a given growth area.

According to a specific embodiment, the growth area is an urban area, e.g., golf courses, athletic fields, parks, cemeteries, roadsides, home gardens/lawns and the like.

According to an additional or alternative embodiment, the growth area is a rural area.

According to an additional or an alternative embodiment, the growth area is an agricultural growth area e.g., open field, greenhouse, plantation, vineyard, orchard and the like.

According to a specific embodiment, the growth area comprises crop plants (e.g., from seeds to full grown plants and anywhere inbetween).

As mentioned, weed control according to the present teachings is effected by reducing fitness of the at least one weed species of interest.

As used herein "fitness" refers to the relative ability of the weed species of interest to develop, reproduce or propagate and transmit its genes to the next generation. As used herein "relative" means in comparison to a weed of the same species not having been artificially pollinated with the pollen of the invention and grown under the same conditions.

It will be appreciated that the effect of pollen treatment according to the present teachings is typically manifested in the first generation after fertilization.

The fitness may be affected by reduction in productiveness, propagation, fertility, fecundity, biomass, biotic stress tolerance, abiotic stress tolerance and/or herbicide resistance.

As used herein "productivity" refers to the potential rate of incorporation or generation of energy or organic matter by an individual, population or trophic unit per unit time per unit area or volume; rate of carbon fixation.

As used herein "fecundity" refers to the potential reproductive capacity of an organism or population, measured by the number of gametes.

According to a specific embodiment, the pollen affects any stage of seed development or germination.

According to a specific embodiment, the reduction in productiveness is manifested by at least one of:
(i) inability to develop an embryo;
(ii) embryo abortion;
(iii) seed non-viability;
(iv) seed that cannot fully develop; and/or
(v) seed that is unable to germinate.

It will be appreciated that when pollen reduces the productiveness, fertility, propagation ability or fecundity of the weed in the next generation it may be referred to by the skilled artisan as sterile pollen, though it fertilizes the weed of interest. Hence, sterile pollen as used herein is still able to fertilize but typically leads to seed developmental arrest or seed abortion.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization and optionally second generation after fertilization and optionally third generation after fertilization.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization.

According to a specific embodiment, reduced fitness results from reduction in tolerance to biotic or abiotic conditions e.g., herbicide resistance.

Non-limiting examples of abiotic stress conditions include, salinity, osmotic stress, drought, water deprivation, excess of water (e.g., flood, waterlogging), etiolation, low temperature (e.g., cold stress), high temperature, heavy metal toxicity, anaerobiosis, nutrient deficiency (e.g., nitrogen deficiency or nitrogen limitation), nutrient excess, atmospheric pollution, herbicide, pesticide and UV irradiation.

Biotic stress is stress that occurs as a result of damage done to plants by other living organisms, such as bacteria, viruses, fungi, parasites, beneficial and harmful insects, weeds, and cultivated or native plants.

Examples of herbicides which are contemplated according to the present teachings, include, but are not limited to, ACCase inhibitors, ALS inhibitors, Photosystem II inhibitors, PSII inhibitor (Ureas and amides), PSII inhibitors (Nitriles), PSI Electron Diverter, PPO inhibitors, Carotenoid biosynthesis inhibitors, HPPD inhibitors, Carotenoid biosynthesis (unknown target), EPSP synthase inhibitors, Glutamine synthase inhibitors, DHP synthase inhibitors, Microtubule inhibitors, Mitosis inhibitors, Long chain fatty acid inhibitors, Cellulose inhibitors, Uncouplers, Lipid Inhibitors (thiocarbamates), Synthetic Auxins, Auxin transport inhibitors, Cell elongation inhibitors, Antimicrotubule mitotic disrupter, Nucleic acid inhibitors or any other form of herbicide site of action.

As used herein "development of flowers" refers to any stage of flowering i.e., from development of non-vegetative organs till anthesis or to fully receptive stigma. Flowers can be unisexual (with either male or female organs) or bisexual (with male stamens and female pistils). Flowering plant species can have separate male and female flowers on the same plant (monoecious) or separate male and female individuals within the population (dioecious).

Specifically, prior to flowering, flower organs are developed to become ready for reproduction. Pre-flowering stages are based on the development of non-vegetative i.e., sexual organs (male part and female part).

The Pre-Flowering stage includes:

1. Pollen Formation—In anther, pollens are formed and developed.

2. Ovary Development—The ovary, the chamber that envelops the ovule, is formed. The tissues in ovule are formed and start developing.

3. Formation of Embryo Sac. The embryo sac, the storage of nutrients for the baby (embryo) to grow until it reaches out of soil and gets own nutrients by photosynthesis, is formed. When the embryo sac is completely developed, the other flower organs are also ready for flowering and fertilization.

Typically a flower is ready for fertilization 1 day prior to flowering. Within the day between pre-flowering and flowering stages, a flower begins pollination.

Once pollen in the anther (male reproductive part) and the embryo sac in the ovule (female reproductive part) are fully developed, the next stage is flowering, i.e., anthesis.

Stigmas of *A. tuberculatus* var. *rudis* unfertilized female flowers can persist indefinitely until pollen reaches them, consistent with observations on another dioecious species, *A. cannabinus* (Quinn et al. J. Torrey Bot. Soc. 127: 83-86 2000). After fertilization, the stigmas dry out. (Costea et al., Canadian Journal of Plant Science, 2005, 85(2): 507-522).

Anthesis is the period during which a flower is fully open and functional. It may also refer to the onset of that period.

According to a specific embodiment, said determining development of flowers comprises determining pre-flowering.

According to a specific embodiment, said determining development of flowers comprises determining development of inflorescence meristem.

According to a specific embodiment, said determining development of flowers comprises determining anthesis.

According to a specific embodiment, said determining development of flowers comprises identification of female structures.

According to a specific embodiment, said determining development of flowers comprises identification of male structures.

According to a specific embodiment, determining flowering is performed once per plant per (weed or crop) growth season.

According to a specific embodiment, determining flowering is performed multiple times per plant or growth area per (weed or crop) growth season. In this case determining is also referred to as "monitoring".

Determining flowering can be effected at the individual level or according to a population level at various regions.

Methods of determining pollination are known in the art.

Conventional methods for determining flowering include dissecting plants under magnification to determine the presence of either a vegetative or reproductive structure at the meristem.

A less time-consuming method often used by plant breeders to determine the flowering is to monitor emergence of the inflorescence, otherwise known as "emergence" or "heading time". Heading time is defined as the moment when the first inflorescence is exerted from the leaf sheaths and becomes visible to the naked eye.

A further method for determining the start of flowering is to monitor anthesis, which is the moment pollen is released from the anthers A widely used method for determining the start of flowering in the field involves repeated visual inspection of plots to estimate the number of flowering plants present in a plot. It is conventionally accepted in agronomics that a plot is "flowering" when 50% of plants in a plot exhibit emerged inflorescences. This technique will give a rough idea as to whether a group of plants is flowering.

US Patent Publication No. 20090226042 teaches a method of determining the point at which a plant starts to flower. Accordingly, this can be effected by determining the start of flowering on an individual plant basis by measuring the reproductive structures of plants from digital images of these structures and deducing the start of flowering from the measurements and average growth rates. Also provided is an apparatus for determining the start of flowering in plants, particularly in a high-throughput manner.

According to an embodiment of the application determining flowering comprises the steps of digitally imaging an inflorescence of a plant; and measuring the inflorescence from the digital image; calculating the flowering (e.g., start of) from the average growth rate of inflorescences and the measurements derived from the calculation.

In this context the term "inflorescence" as used herein is taken to broadly mean a reproductive structure. The form of the inflorescence may vary depending on the plant species in question, however a person skilled in the art would be well aware of the relevant structure(s) to be measured.

Advantageously, the method of this embodiment of the invention allows the start of flowering to be accurately determined on an individual plant level.

Furthermore, this method provides means to discriminate flowering and non-flowering plants from the presence or absence of an inflorescence.

The dimensions (typically the area, but this may also be the length and/or width) of the inflorescence is measured from the digital image and using this information and the average growth rate for inflorescences (of the plant species or variety in question) one may back calculate the point of emergence of the inflorescence.

According to embodiments of the invention and this embodiment in particular determining development of flowers is effected by integrating plant data and/or field data with literature data such as will be apparent infra.

For example, the average growth rate of an inflorescence of a particular plant species or variety is 10 cm per day, and the observed size of an inflorescence of a plant of the same species or variety is 30 cm, therefore it can be deduced that the inflorescence appeared 3 days before the moment of the observation. Therefore the start of flowering would also have been 3 days before the moment of the observation.

According to an embodiment of the invention, to determine flowering requires a detectable and measurable inflorescence to be present at the time of imaging, however this need not be the first inflorescence. Thus contemplated is measuring flowering of first inflorescence, second inflorescence etc. Furthermore, the inflorescence should not have reached its maximum size at the time of imaging. This would require observations of a sufficient frequency so that at least one observation is performed between emergence of the inflorescence and before it reaches its maximum size. The frequency of observations can readily be determined by a person skilled in the art and will of course depend upon the species or variety in question.

Such a method is particularly suited to handling large numbers of plants in a high throughput manner, whilst retaining a high level of accuracy, since flowering can be determined on an individual plant level.

According to a specific embodiment, determining at the level of an individual plant is also advantageous for weed in which flowering is synchronized such as due to environmental reasons. For instance, synchronized flowering is taken place in *Amaranthus palmeri* (*A. Palmeri*) weed. Korres and Norsworthy (2017), Weed Science, 65(4):491-503 conducted field experiments in Arkansas University during the summers of 2014 and 2015 and they investigated *A. palmeri* flowering initiation and progress. According to their observations *A. palmeri* weed emerges at late June and its flowering initiation starts at the end of July or the beginning of August (about 30-40 days after emergence) and continues for approximately 40-50 days. In addition, it has been demonstrated that the flowering period of *A. palmeri* population is relatively synchronized and it is independent from the plant emergence date as it is regulated by environmental conditions such as day length and temperature (Keeley et. Al, 1987; Weed Science Vol. 35, No. 2 (March, 1987), pp. 199-204; Korres and Norsworthy (2017), Weed Science, 65(4):491-503; Clay et al., 2016; Weed Science Society of America, Annual Meeting. San Juan, Puerto Rico, Feb. 8-11, 2016). Similar observations regarding flowering synchronization were also reported for *A. tuberculatus* (Wu and Owen, 2014; Weed Science, 62(1):107-117). Hence, integrating field data which determines a pre-flowering stage such as described above is sufficient together with literature data to determine anthesis and pollinating at the relevant stage.

Such methods can be performed using an apparatus for determining flowering, which apparatus typically comprises one or more digital cameras with sufficient resolution for imaging emerging plant inflorescences; and computer means for detecting and measuring plant inflorescences and for deriving the start of flowering from said measurements and average growth rates of inflorescences.

Determining flowering can be effected in situ (e.g., in the field).

In this case, one or more digital cameras are arranged to move over the plants to take images of the plant inflorescences.

According to a specific embodiment, plants are presented to the camera in such a way that individual plants can be discriminated and identified. This allows assessment of population homogeneity for flowering time using existing statistical techniques. Digital cameras suitable for imaging emerging plant inflorescences are typically those allowing the inflorescences imaged to have a minimum size of about 100 pixels.

The computer means for detecting and measuring plant inflorescences comprises image-processing software. Typically, such software uses features specific to inflorescences to distinguish these from, say, vegetative organs (stems and leaves). For example, flowers often exhibit a different color and/or texture than the rest of the plant. Rollin et al., 2016 discusses (Rollin, O., Benelli, G., Benvenuti, S. et al. Agron. Sustain. Dev. (2016) 36: 8.) that flower shape and color play a key role in routing insect foraging flights (Menzel and Shmida 1993). Many *Brassicaceae* species reflect ultraviolet radiation to attract insect pollinators (Yoshioka et al. 2005). These can be used in a similar way for detection purposes.

For instance, where the range of colors displayed by immature inflorescences is close to that of stems or leaves, the software uses differences in shape and pattern to distinguish from the more granular structure of the inflorescence which results in a higher pixel-to-pixel variation than that of the leaves or stem. Topological cues can also be used to refine detection. For example, inflorescences are usually found at the top of the plant and they are always connected to a stem.

An example of digital images processing of images of weed plants from which the plant inflorescences may be measured. A starting image is subjected to a so-called "thresholding" process involves removal of all non-plant parts. Thresholding is achieved by virtue of the background and non-plant parts exhibiting a different color range to the plant organs. After that an image after thresholding is produced. This is followed by a statistical method termed "color variation analysis" which is applied to the remaining pixels to determine which parts exhibit textural properties akin to that of inflorescences. An image after color variation analysis is prepared. Literature data of inflorescence color and texture would be required for this step, Objects classified as "non-inflorescence" through the process of color variation analysis are removed. Finally, the dimensions of the remaining objects, classified as "inflorescences", are recorded by the software. Since some parts of the inflorescences can be hidden by other plant parts, such as leaves, it is preferable to refine the measurements by averaging the results obtained from several pictures, say at least 3 pictures or images and generally not more than 6.

Statistical analysis may also be carried out on data collected using the unique identifier. For example, statistical data analysis to determine the start of flowering may be based on the following three steps. The first step corrects for the presence of an inflorescence based on logic rules, i.e. assumes that there is consistency between the six pictures or images taken of any one image, that there are no inflorescences on plants that are smaller than a certain size and that inflorescences do not disappear once present. The second step estimates the speed of inflorescence growth in the entire batch of plants. In this step, inflorescence size is corrected for plant size, an exponential inflorescence growth is assumed in the first week of growth and a date for inflorescence emergence is estimated for each plant. In the third step, population means of the inflorescence emergence date and standard errors on these estimates are calculated based on survival method (Cox models).

If, for example, plants are imaged at weekly intervals, the presence of an inflorescence on an image allows the start of flowering to be determined with a resolution of one week. More thorough data analysis making use of inflorescence size may be used to interpolate between two images and to determine the start of flowering with a lower resolution for individual plants More thorough data analysis making use of inflorescence size may also be used to provide more reliable estimates of the mean start of flowering for a population of plants considering the presence of plants that were not flowering at the time of last imaging.

Additional information may be recorded such as species (e.g., based on light reflectance), date, inflorescence measurements and/or other measurements (e.g., height, plants per plot, density, distribution, geographical location, male and/or female organs), and any other quantitative or qualitative observations made on the plant. Data contained in the database can be retrieved by means of appropriate software.

Molecular determination of transition to flowering such as LEAFY and APETALA 1 in *A. thaliana* and their respective homologoues FLORICAULA and SQUAMOSA in *A. majus* (Krizek and Fletcher nature reviews genetics 2005).

Additional information will include identification depending on floral odor and fragrance and relies on volatiles such as described in Schiestl and Marion Poll., 2002.

Therefore, chemical determination of flowering can be used for detection. In Rollin et al., 2016 (Rollin, O., Benelli, G., Benvenuti, S. et al. Agron. Sustain. Dev. (2016) 36: 8.) olfactory and tactile cues were discussed as insect recognition patterns that can be used also for detection purposes. A mechanism for identification and recognition of flowers also consists in the production and emission of volatile compounds, mainly terpenoids and benzenoids (van Schie et al. 2006). The two dominant components of the fragrance of *Cirsium* species (Asteraceae), benzaldehyde and phenylacetaldehyde, attract several orders of generalist insect pollinators (Theis 2006). Fragrance of their flowers is emitted in dynamic patterns that maximize pollinator attraction (Theis et al. 2007).

Determination of flowering based on pollen in the air in the growth area is also another measure. The skilled in the art would know how to determine air pollen. For instance, Burkard volumetric spore trap, which vacuums up air through a slit and captures floating grains. Pollen count can also be measured by attaching a rotating rod with a sticky substance. After 24 hours, the amount of pollen that has adhered to the rod is analyzed.

Yet another method is determining vegetative portions which are often indicative of later flowering. For instance by counting the number of leaves, which in some weed species is indicative of flowering.

An aspect of some embodiments of the present invention relate to system, an apparatus, methods, and/or code instructions (stored on a data storage device, executable by one or more hardware processors) for reducing fitness of at least one weed species of interest. Images(s) including one or more weeds specie of interest are fed into a classifier(s). The classifier(s) compute an indication of likelihood of the weed(s) being at a target growth state suitable for artificial pollination of flowers of the weed(s) species of interest at a certain time interval. The certain time interval may represent a current time and/or a future time. Instructions are generated according to the likelihood indication and the certain time interval. The instructions are for execution by a pollination controller of a pollinator device for artificially pollinating flowers of the weed(s) species of interest with pollen that reduces fitness of the at least one weed species of interest.

The classifier(s) is trained on a training dataset that includes multiple images. Each image includes one or more weeds of one or more species of interest. Each image is associated with an indication of a time interval of when the respective weed(s) species of interest reaches at the target growth state suitable for artificial pollination of flowers thereof relative to the time of capture of the respective image.

Optionally, the at least one image captured by the imaging sensor depicts the weed(s) species of interest at a growth stage prior the start of flowering. In such a case, when the target growth state is after the start of flowering, the future time interval when the target growth state is reached is predicted based on the image depicting the weed prior to the start of flowering.

The target growth state suitable for artificial pollination of flowers of the weed(s) species of interest refers to any stage of growth of the weed, which may vary according to type of weed (e.g., weed species) and/or according to the type of artificial pollination (e.g., different types of artificial pollen may be designed to work for different growth states of different weeds). For example, stage of flowering i.e., from development of non-vegetative organs till anthesis, such as pre-flowering stages described herein.

Some implementations of the systems, methods, apparatus, and/or code instructions described herein relate to the technical problem of reducing fitness of weeds.

Some implementations of the systems, methods, apparatus, and/or code instructions described herein improve the technological field of reducing fitness of weeds.

In some implementations the improvements are based on real-time identification of weeds being at a target growth state, and artificial pollination of flowers of the weed(s) species of interest with pollen that reduces fitness of the weed(s) species of interest. For example, ground based machinery, aerial based machinery, a land based and/or aerial vehicle (e.g., tractor, drone) may navigate over the field, where for each location of the field, weeds at a target growth state suitable for artificial pollination with pollen that reduces fitness of the weeds are automatically identified and pollinated in real time. In another example, stationary cameras monitor the field to identify weeds at a target growth state, and machinery (e.g., vehicle) is dispatched to the locations within the field at which the weeds were identified to pollinate the weeds to reduce fitness thereof.

As used herein, the term machinery may refer to ground based machinery and/or aerial based machinery, as described herein.

The pollinator device described herein may sometimes be interchanged with the term precision agricultural tools, as described herein. The pollinator device described herein may be implemented as and/or may include, for example, as the precision agricultural tool(s), as described herein.

In other implementations, the improvements are based a prediction of a future time interval during which weeds reach the target growth state, and pollinating the weeds when the future time interval is reached. That is, the weed does not necessarily need to be presently at the target growth state suitable for pollination, but rather at an early growth state. The future time interval at which the weed is expected to reach the target growth state is predicted, allowing for advanced planning of the pollination of the weeds. For example, images are acquired on day 1, with a prediction that the weeds will reach the state suitable for artificial pollination on day 10. The identification and pollination may be performed by separate stationary fixtures and/or by separate mobile machinery (e.g., vehicles). For example, aerial based machinery (e.g., a drone) may fly over the field capturing images on day 1, and the ground based machinery (e.g., tractor) with pollinator device (e.g., precision agricultural tool) may drive over the field to pollinate the weeds on day 10 according to the generated instructions.

In yet other implementations, the improvements are based on a non-conventional use of location data outputted by a location sensor, to tag the location of the image that depicts the identified weed at the present or future growth state suitable for artificial pollination for fitness reduction thereof, and guiding the pollination device for pollinating the geographic location of the identified weed according to the location data. For example, a drone may fly over the field capturing images on day 1, that include the geographic location of each captured image. The tractor with pollinator device may drive over the field to pollinate the weeds on day 10 (or multiple other days), guided by the geographic locations of the captured images.

The instructions for pollination may be adjusted according to different geographic locations, for example, according to the density and/or number of weeds and/or species of weeds appearing in each image corresponding to the different geographic locations. For example, one region of a field is pollinated with a small volume to treat one weed, and another region of the field is pollinated with a large volume to treat multiple weeds.

Determining flowering and/or pollination can be determined manually.

Determining flowering and/or pollination can be determined using ground machinery.

Determining flowering and/or pollination can be determined using aerial machinery.

Regardless of the method, once flowering is determined and the time frame for pollination deduced, the weed is subjected to artificial pollination.

According to a specific embodiment, determining flowering and/or pollination can be determined using a combination of aerial machinery, ground machinery and/or manually According to a specific embodiment, when using ground machinery, it is preferably adapted not to affect the crop plants at the growth area.

For instance, according to a specific embodiment, crop height is taken into consideration. An illustrative example is provided. Machinery in the field during Palmer Amaranth flowering: During this flowering period (Late July to September, Arkansas, Korres and Norseworthy., 2017) crop height is high. Corn full size can reach at least 1.2 meter, soybean is around 60-80 cm and cotton is around 75-110 cm. This fact dictates the type of tools that can be used.

According to a non-limiting embodiment, the ground equipment that is available for use in fields during this period is the 'High-clearance' tractors that have a high frame structure (50-80 inches height) that allow in-crop spraying without injuring the crop, e.g., High clearance tractors by Hagie and Case IH or such tractors by Miller can be used in-season spraying while crop is high.

These tractors are manufactured by several companies such as Hagie, Case IH and Miller. In addition, such tractors are equipped with a 'boom height control system' that enables automatic control of spraying height above the ground and the crop. These systems optimize spraying positioning and minimize crop injury while spraying.

Conversely, aerial application accounts for almost 20% of all applied crop protection products on commercial farms in the US. According to a USDA Economic Research Service Report, 71 million acres (out of 286 million acres of cropland in the US) is treated aerially every year. While corn and soybean are among the five most commonly treated crops by aerial applicator operators. (www(dot)agaviation (dot)org/industryfacts). Thus, aerial application can be used to determine flowering/pollinate in the field during the correct time without injuring the crop.

Additional tools that can be used include more advanced tools such as unmanned aerial vehicles (UAV), remote-piloted vehicles(RPV), drones or specialized robots.

Another potential application methodology includes the use of:

1. Insects e.g., honey bees (for pollination);

2. bee vectoring technology (BVT), employing an inoculum dispenser system that is incorporated into the lid of a commercial bee hive. Commercially-reared bees enter the dispenser through a one-way return flap and exit through another portal. As they do so, they pass through and pick up powder material (in this case weed pollen) in BVT's Vectorpak™, taking it with them as they leave the hive (www (dot)beevt(dot)com/about/);

3. robot bee-actually referring to pollination drawns (www(dot)cbinsightsdotcom/research/walmart-farming-drones-patent/?utm_source=_CB+_Insights+_Newsletter& utm_c_amp_aign=_2edf6b_8381-TuesNL_03_20_2018&utm_medium=_email&utm_term=_0_9dc0513989-2edf6b_8381-87383133, 4. robobees (wyss(dot)harvard(dot)edu/technology/autonomous-flying-microrobots-robobees/);

5. robo-bee (www(dot)npr(dot)org/sections/thesalt/2017/03/03/517785082/rise-of-the-robot-bees-tiny-drones-turned-into-artificial-pollinators).

In all of these methods bees or robots/drones mimicking bees display the pollen in either an undirected or directed way onto weed flowering plants or specifically weed flowering female plants in the field.

According to a specific embodiment, pollinating is effected at stigma receptive stage.

According to a specific embodiment, pollinating is effected at anthesis.

According to a specific embodiment, pollinating is effected prior to anthesis but once the stigma is receptive.

According to a specific embodiment, pollinating is effected once per crop (that is present in the field) growth season.

According to a specific embodiment, pollinating is effected a number of times (e.g., 1-150 times) per (weed or crop) growth season.

According to a specific embodiment, pollinating is effected prior to or at anthesis.

Each of the determining flowering and/or pollinating can be effected more than once per plot. For instance, pollination can be effected post crop emergence and prior to crop harvesting. For instance, in the weeds *Amaranthus palmeri* and *Amaranthus tuberculatus* interfering in a corn, soybean or cotton field pollination will be applied during late season. Alternatively or additionally, after crop harvesting in order to avoid seedbank replenishment. Each and any of the above tools can be coupled to an agricultural precision tool.

Precision agriculture (PA), satellite farming or site specific crop management (SSCM) is a farming management concept based on observing, measuring and responding to inter and intra-field variability in crops. The goal of precision agriculture research is to define a decision support system (DSS) for whole farm management with the goal of optimizing returns on inputs while preserving resources.

Among these many approaches is a phytogeomorphological approach which ties multi-year crop growth stability/characteristics to topological terrain attributes. The interest in the phytogeomorphological approach stems from the fact that the geomorphology component typically dictates the hydrology of the farm field.

The practice of precision agriculture has been enabled by the advent of GPS and GNSS. The farmer's and/or researcher's ability to locate their precise position in a field allows for the creation of maps of the spatial variability of as many variables as can be measured (e.g. crop yield, terrain features/topography, organic matter content, moisture levels, nitrogen levels, pH, EC, Mg, K, and others). Similar data is collected by sensor arrays mounted on GPS-equipped combine harvesters. These arrays consist of real-time sensors that measure everything from chlorophyll levels to plant water status, along with multispectral imagery. This data is used in conjunction with satellite imagery by variable rate technology (VRT) including seeders, sprayers, etc. to optimally distribute resources.

Precision agriculture has also been enabled by unmanned aerial vehicles like the DJI Phantom which are relatively inexpensive and can be operated by novice pilots. These systems, commonly known as drones, can be equipped with hyperspectral or RGB cameras to capture many images of a field that can be processed using photogrammetric methods to create orthophotos and NDVI maps.

According to a specific embodiment, the use of a technique called multispectral analysis is used. This technique looks at how strongly plants absorb or reflect different wavelengths of sunlight, they can discover which weed are flowering and which not.

Sensors attached to moving machinery (ground or aerial) can even take measurements on the run. For example, multispectral sensors mounted on a tractor's spraying booms.

Thus, data can be collected on the go i.e., in real time while treating the crop/weed.

Alternatively, pollinating can be effected based on data deduced from former measurements.

As used herein "pollen" refers to viable pollen that is able to fertilize the weed species of interest and therefore competes with native pollination.

Alternatively, when native pollen competition does not exist, or very low levels of native pollen are present, pollination by the designed pollen inhibits apomixis of weeds and by this reduces their quantities as well [Ribeiro et al. 2012 Abstracts of the Weed Science Society of America Annual Meeting. www(dot)wssaabstracts(dot)com/public/9/abstract-438(dot)html].

According to a specific embodiment, the pollen is of the same species as of the target weed (e.g., invasive, aggressive weed).

According to a specific embodiment, the pollen exhibits susceptibility to a single growth condition e.g., herbicide, temperature.

According to a specific embodiment, the pollen exhibits susceptibility to multiple growth conditions e.g., different herbicides.

According to a specific embodiment, the pollen is non-genetically modified.

The pollen may therefore be of a naturally occurring plant that reduces the fitness of the at least one weed species of interest. According to a specific embodiment, *A. palmeri* or *A. tuberculatus* susceptible seeds are available from the Agriculture Research Service National Plant Germplasm System plant introduction (USDA-ARS_NPGS PI) as well as from various locations in Israel.

Alternatively or additionally, the pollen may be of a plant that has been selected towards producing pollen that reduces the fitness of the at least one weed species of interest.

Selection can be effected by way of exposing the weed to various concentrations of, for example, a herbicide or a plurality of different herbicides, and selecting individuals which show increased susceptibility to the herbicide or different herbicides. Alternatively or additionally, different plants exhibiting susceptibility to different herbicides can be crossed to generate a plant exhibiting susceptibility to a number of herbicides of interest.

It will be appreciated that such breeding need not engage into pedigree breeding programs as the mere product is the pollen of a weedy plant.

According to a specific embodiment, there is provided a method of producing pollen that reduces fitness of at least one weed species of interest, the method comprising treating the weed species of interest (e.g., seeds, seedlings, tissue/cells) or pollen thereof with an agent that reduces fitness.

When needed (such as when treating that weed (e.g., seeds, seedlings, tissue/cells) the method further comprises growing or regenerating the plant so as to produce pollen.

According to a specific embodiment, the method comprises harvesting pollen from the weed species of interest following treating with the agent that reduces the fitness.

It will be appreciated that the pollen may be first harvested and then treated with the agent (e.g., radiation) that reduces the fitness of the weed species of interest.

Alternatively or additionally, the pollen is produced from a plant having an imbalanced chromosome number (genetic load) with the weed species of interest.

Thus, for example, when the weed of interest is diploid, the plant producing the pollen is treated with an agent rendering it polyploid, typically, tetraploids are selected, such that upon fertilization with the diploid female plant an aborted or developmentally arrested, not viable seed set are created. Alternatively, a genomically imbalanced plant is produced which rarely produces a seed set.

According to a specific embodiment, the weed (or a regenerating part thereof or the pollen) is subjected to a polyploidization protocol using a polyploidy inducing agent, that produces plants which are able to cross but result in reduced productiveness, Thus, according to some embodiments of the invention, the polyploid weed has a higher chromosome number than the wild type weed species (e.g., at least one chromosome set or portions thereof) such as for example two folds greater amount of genetic material (i.e., chromosomes) as compared to the wild type weed. Induction of polyploidy is typically performed by subjecting a weed tissue (e.g., seed) to a G2/M cycle inhibitor.

Typically, the G2/M cycle inhibitor comprises a microtubule polymerization inhibitor.

Examples of microtubule cycle inhibitors include, but are not limited to oryzalin, colchicine, colcemid, trifluralin, benzimidazole carbamates (e.g. nocodazole, oncodazole, mebendazole, R 17934, MBC), o-isopropyl N-phenyl carbamate, chloroisopropyl N-phenyl carbamate, amiprophos-methyl, taxol, vinblastine, griseofulvin, caffeine, bis-ANS, maytansine, vinbalstine, vinblastine sulphate and podophyllotoxin.

According to a specific embodiment, the microtubule cycle inhibitor is colchicine.

Still alternatively or additionally, the weed may be selected producing pollen that reduces fitness of the weed species of interest by way of subjecting it to a mutagenizing agent and if needed further steps of breeding.

Thus, weed can be exposed to a mutagen or stress followed by selection for the desired phenotype (e.g., pollen sterility, herbicide susceptibility).

Examples of stress conditions which can be used according to some embodiments of the invention include, but are not limited to, X-ray radiation, gamma radiation, particle irradiation such as alpha, beta or other accelerated particle, UV radiation or alkylating agents such as NEU, EMS, NMU and the like. The skilled artisan will know which agent to select.

According to a specific embodiment, the stress is selected from the group consisting of X-ray radiation, gamma radiation, UV radiation. For example. pollen of the weed can be treated with the agent that reduces the fitness (e.g., radiation) following harvest.

Guidelines for plant mutagenesis are provided in K Lindsey Plant Tissue Culture Manual—Supplement 7: Fundamentals and Applications, 1991, which is hereby incorporated in its entirety.

Other mutagenizing agents include, but are not limited to, alpha radiation, beta radiation, neutron rays, heating, nucleases, free radicals such as but not limited to hydrogen peroxide, cross linking agents, alkylating agents, BOAA, DES, DMS, EI, ENH, MNH, NMH Nitrous acid, bisulfate, base analogs, hydroxyl amine, 2-Naphthylamine or aflatoxins.

Alternatively or additionally, the pollen may be genetically modified pollen (e.g., transgenic pollen, DNA-editing).

Numerous methods are known for exploiting genetic modification to render it suitable for reducing the fitness of a weed species of interest.

Thus, according to a specific embodiment, the pollen is genetically modified pollen.

According to other specific embodiments, the trait being inherited upon artificial pollination with the pollen of the invention is selected from the group consisting of embryo abortion, seed non-viability, seeds with structural defects, seeds that are unable to germinate, abiotic/biotic stress susceptibility (e.g., herbicide susceptibility) or induced death or sensitivity upon chemical or physical induction or any other inherited property that will enable controlled reduction of weed population size.

Often sterile pollen results in a seedless plant. A plant is considered seedless if it is not able to produce seeds, traces of aborted seeds or a much-reduced number of seeds. In other cases the pollen will produce plants with seeds that are unable to germinate or develop e.g., no embryo or embryo abortion.

According to a specific embodiment, the pollen is genetically modified to express an exogenous transgene that upon fertilization will reduce fitness of the weed of interest (next generation). Such a gene is termed a "disrupter gene". According to some embodiments, the disrupter gene causes kills the weed species of interest, accordingly it is termed a "death gene".

According to a specific embodiment, the pollen is genetically modified to express a silencing agent that upon fertilization will reduce fitness of the weed of interest (next generation).

According to a specific embodiment, the pollen is genetically modified to express a genome editing agent that upon fertilization will reduce fitness of the weed of interest (next generation).

In some embodiments of the invention, the genetic modification is effected in an inducible manner to minimize the effect on the weed producing the pollen product of the invention (i.e., that reduces the fitness of the plant of interest).

Genetic Use Restriction Technology (GURT).

Embodiments of the invention make use of this technology which provides specific genetic switch mechanisms that hamper reproduction (variety specific V-GURT) or the expression of a trait (trait-specific T-GURT) in a genetically modified (transgenic) plant.

Variety GURT (also known as suicide/sterile seed/gene technology or terminator technology) is designed to control plant fertility or seed development through a genetic process triggered by a chemical inducer that will allow the plant to grow and to form seeds, but will cause the embryo of each of those seeds to produce a cell toxin that will prevent its germination if replanted, thus causing second generation seeds that will not germinate.

T-GURT (ironically known as traitor technology) is designed to switch on or off a trait (such as herbicide/cold/drought/stress tolerance, pest resistance, germination, flowering or defense mechanisms) using inducible promoters regulating the expression of the transgene through induced gene silencing (e.g., by antisense suppression) or by excision of the transgene using a recombinase. In this case, the genetic modification is activated by a chemical treatment or by physical factors e.g., environmental factors such as heat.

These methods are reviewed by Lombardo 2014 Plant Biotechnology Journal 12:995-1005, U.S. Pat. No. 5,364,780, WO9403619, WO9404393, U.S. Pat. No. 5,723,765 each of which is incorporated herein by reference.

Both methods can rely on site-specific recombination of DNA in plant cells. Typically the recombination system employed is from bacteriophage P1. The system comprises a recombinase (Cre) and recombination sites (loxP). In the presence of Cre, recombination between loc sites occurs on supercoiled, nicked, circular or linear DNA. Alternative recombination systems are: Flp/frt, R/RS, Gin/Gix. Specific signal sequences can be selected from the group comprising LOX sequences and sequences recognizable by either flippase, resolvase, FLP, SSV1-encoded integrase, or transposase and the second gene that encodes a specific recombinase can be selected from the group comprising CRE, flippase, resolvase, FLP, SSV1-encoded integrase, and transposase.

The activation of a cytotoxic gene using this system is a well known way of producing sterile plants.

For V-GURTs, essentially three different restriction mechanisms are proposed (Visser et al., 2001 Biotechnol. Dev. Monit. 48, 9-12). The first mechanism of action is that described in the patent (U.S. Pat. No. 5,723,765) by the USDA and Delta & Pine Land (nominally the first V-GURT). This GURT is based on the transfer of a combination of three genes (transgenes), two derived from bacteria and one from another plant, into a plant's cells:

1. A gene coding for a cytotoxic protein (the terminator or lethal gene) e.g., under control of a late embryogenesis abundant (LEA) promoter linked to a DNA spacer (blocking) sequence flanked by specific excision sites (lox sequence) that prevents the activation of the terminator gene. In the '765 patent, the cytotoxic protein is the ribosome inactivating protein (RIP), otherwise known as saporin derived from *Saponaria officinalis*, which prevents plant cells from synthesizing proteins. Barnase is an alternative for RIP, as will be further described hereinbelow;

2. A site-specific recombinase gene under the control of a constitutively active promoter (e.g., CaMV 35S) containing one or more tet operons that is subject to repression by the Tet repressor. This gene encodes a recombinase (e.g., Cre)

that cuts the specific excision sites flanking the blocking sequence linked to the toxic gene;

3. A repressor gene (e.g., Tn10 tet) under the control of a constitutive promoter and encoding a protein that binds to the responsive operon (e.g., tet), preventing the expression of the recombinase gene. The presence of an external stimulus (chemical or physical inducer) prevents binding of the repressor to the operon. The external stimulus can be chemical inducers such as agrochemicals and antibiotics or physical such as temperature.

In another embodiment of the method, which is also contemplated herein, the recombinase gene is directly linked to an inducible promoter (U.S. Pat. No. 5,723,765).

Potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide [Reviewed in Padidam et al., 2003].

It will be appreciated that in sharp contrast to prior art methods, the genetically modified pollen is that of the weed and not that of the crop.

U.S. Pat. No. 5,925,808 describes embodiments of the Genetic Use Restriction Technology, and is hereby incorporated by reference in its entirety.

Following is a non-limiting example, for the use of GURT in conferring weeds with reduced fitness.

Thus, the following constructs can be produced.

1. A gene which expression results in an altered plant phenotype e.g., disrupter gene, linked to a transiently active promoter, the gene and promoter being separated by a blocking sequence flanked on either side by specific excision sequences.

2. A second gene that encodes a recombinase specific for the specific excision sequences linked to a repressible promoter.

3. A third gene that encodes the repressor specific for the repressible promoter.

Plasmid sequences and procedures can be used as described in U.S. Pat. No. 5,925,808, supra:

According to an exemplary embodiment, the death gene used is RIP (ribosomal inhibitor protein, sequence of a complete RIP gene, saporin 6: GenBank ID SOSAP6, Accession No. X15655) or barnase (Genbank Accession M14442). The CRE Gene is under the control of a Tetracycline-derepressible 35S Promoter. The third plasmid comprises a Tet Repressor Gene Driven by a 35S Promoter.

The transiently active promoter in the first plasmid is expressed during embryogenesis, seed development or seed germination. Optional gene promoters include promoters of embryogenesis genes such as late embryogenesis abundant genes LEA1, LEA2, LEA5, LEA4, LEA5, DEHYDRIN and SMP (Pedrosa et al., 2015), promoters of seed development genes such as LEAFY COTYLEDON genes, including, but not limited to, LEC1, LEC2 and FUSCA3 (FUS3), or ABSCISIC ACID INSENSITIVE 3 (ABI3) (Santos-Mendoza et al., 2008). Additional promoters of seed development genes can be taken from multiple comprehensive studies that identified a long list of related genes (see Le et al., 2010 and McElver J et al., 2001). Promoters of Germination genes include but are not limited to Expansin (Chen and Bradford., 2000), endo-β-mannase (Nonogaki H et al., 2000), β-1,3-glucanase (Leubner-Metzger and Meins, 2000 and Wu et al., 2001), extension like protein ERP1 (Dubreucq et al., 2000) as well as genes that are related to abscisic acid (ABA) and gibberellic acid (GA) biosynthesis (Shu et al., 2015 and Toorop et al., 2000).

Other construct systems which can be used rely on a transcriptional inducible system. In such constructs, transcription is reversibly turned on or off in the presence of an analyte e.g., antibiotic e.g., tetracycline or one of its derivatives (e.g. doxycycline). Such are described in Wikipedia and is summarized infra. Briefly, the Tet-Off system makes use of the tetracycline transactivator (tTA) protein, which is created by fusing one protein, TetR (tetracycline repressor), found in *Escherichia coli* bacteria, with the activation domain of another protein, VP16, found in the Herpes Simplex Virus.

The resulting tTA protein is able to bind to DNA at specific TetO operator sequences. In most Tet-Off systems, several repeats of such TetO sequences are positioned upstream of a minimal promoter. The entirety of several TetO sequences with a minimal promoter is called a tetracycline response element (TRE), because it responds to binding of the tetracycline transactivator protein (tTA) by increased expression of the gene or genes downstream of its promoter. In a Tet-Off system, expression of TRE-controlled genes can be repressed by tetracycline and its derivatives (e.g., doxycycline, anhydrotetracycline). They bind tTA and render it incapable of binding to TRE sequences, thereby preventing transactivation of TRE-controlled genes. A Tet-On system works similarly, but in the opposite fashion. While in a Tet-Off system, tTA is capable of binding the operator only if not bound to tetracycline or one of its derivatives, such as doxycycline, in a Tet-On system, the reverse tetracycline transactivator (rtTA) protein is capable of binding the operator only if bound by a tetracycline. Thus, the introduction of doxycycline to the system initiates the transcription of the genetic product.

Examples for use of these systems include but not limited to the following set of constructs that relies on the Tet ON system:

1. A gene which expression results in an altered plant phenotype linked to a transiently active promoter, the gene and promoter being separated by a blocking sequence flanked on either side by specific excision sequences.

2. A second gene that encodes a recombinase specific for the specific excision sequences linked to an operator that is upstream to the promoter and is responsive to an activator.

3. A third gene that encodes the activator specific for the operator in the second plasmid under a constitutive promoter.

Applied inducer binds the activator protein eliciting a conformational change to its active form.

According to an exemplary embodiment, the death gene used under the control of an embryogenesis, seed development or seed germination promoter is RIP (ribosomal inhibitor protein, sequence of a complete RIP gene, saporin 6:GenBank ID SOSAP6, Accession No. X15655) or barnase (Genbank Accession M14442). The CRE Gene is under the control of a Tet-ON TRE and the third plasmid is a constitutive promoter upstream of an rtTA. Upon application of tetracycline or its derivatives such as doxycycline the rtTA becomes activated and results in expression of the CRE recombinase and consequently activates the death gene.

Another optional set of plasmids that can be used is a simplified two plasmids system that again relies on the Tet-ON system:

1. A gene which expression results in an altered plant phenotype linked to a transiently active promoter and an operator that is upstream to the promoter and is responsive to an activator.

2. A second gene that encodes the activator specific for the operator from the first plasmid under a constitutive promoter.

According to an exemplary embodiment, the death gene used is RIP (ribosomal inhibitor protein, sequence of a complete RIP gene, saporin 6:GenBank ID SOSAP6, Accession No. X15655) or barnase (Genbank Accession M14442). The death gene is under the dual control of both a promoter that is active during embryogenesis, seed development or seed germination as well as a Tet-ON TRE.

And the second plasmid is a constitutive promoter upstream of an rtTA. Upon application of tetracycline or its derivatives such as doxycycline the rtTA becomes activated and results in activation of the death gene.

Yet alternatively or additionally, plants which produce pollen capable of reducing fitness of a weed species of interest can be generated by a hybrid GURT method whereby a dual complementary male and female plant genetic recombination systems are used.

A weed sterile line is being produced by crossing between two homozygous transformed plants. The male and female plants are each transformed with a plasmid encoding a disrupter gene controlled by a transiently active promoter, the gene and promoter being separated by a blocking sequence flanked on either side by specific excision sequences (such as lox or frt excision sequences). In addition the plasmid contains a second gene that encodes a genetic recombination enzyme (such as cre recombinase or flp flippase) specific for the excision sequences in the opposite sex (namely, the recombination enzyme of the female plant cut the excision sequence in the male and vice versa). These recombination enzymes are under the control of a promoter that is active post seed germination stage. The transformed plasmid both in the male and in the female homozygous lines are inserted to the same genomic locus position.

The following plasmid is transformed into the female plant:

Plasmid encoding a barnase or RIP gene under the control of a specific embryogenesis, seed development or germination promoter whereas the gene and promoter being separated by a blocking sequence flanked on either side by specific excision lox sequences and a second gene encoding for a flippase recombination enzyme under a promoter that is active post seed germination.

The following plasmid is transformed into the male plant:

Plasmid encoding a barnase or RIP gene under the control of a specific embryogenesis, seed development or germination promoter whereas the gene and promoter are being separated by a blocking sequence flanked on either side by specific excision frt sequences and a second gene encoding for a cre recombinase recombination enzyme under a promoter that is active post seed germination.

Lines are being selected such that both insertions to both male and female are on the exact same genomic position.

Only upon crossing between these male plants with these female plants both recombination events by flp and cre are occurring thus yielding pollen that have a barnase or RIP gene under the control of a specific embryogenesis, seed development or germination promoter.

Another embodiment of V-GURT contemplated herein (see U.S. Pat. No. 5,808,034, herein incorporated in its entirety) is based on a reversed process because it is characterized by the presence of a gene encoding a disrupter protein that is active in embryogenesis seed development or seed germination thus resulting in loss of productiveness. Only upon exposure to a chemical or physical inducer that result in inhibition of the disrupter gene the plant is capable of reproducing normally. It will be appreciated that in sharp contrast to prior art methods, the genetically modified pollen contains the disrupter gene under the regulation of a transiently active promoter that is expressed during embryogenesis, seed development or seed germination and not male flower specific promoters.

Thus, a sterile line can be produced using two plasmids:

1. Plasmid encoding for a disrupter protein under a promoter that is active in the embryo or seed, which makes it sterile where the gene promoter is under the control of a specific operator sequence responsive to repression by a repressor protein.

2. A repressor protein, whose gene is under the control of a constitutive promoter. When binding to a specific chemical the repressor can bind the operator from the first plasmid and inhibit the expression of the disrupter protein. According to an exemplary embodiment, the disrupter gene used under the control of an embryogenesis, seed development or seed germination promoter as well as the control of at least one TetO element is RIP (ribosomal inhibitor protein, sequence of a complete RIP gene, saporin 6:GenBank ID SOSAP6, Accession No. X15655) or barnase (Genbank Accession M14442). The reverse TetR gene (mutated form of the original TetR) is under a constitutive promoter. Upon application of tetracycline or its derivatives such as doxycycline the reverse TetR becomes activated and results in inhibition of expression of the disrupter induced gene.

Alternatively, it can be produced by using the Tet-Off system with the following two plasmids:

1. Plasmid encoding for a disrupter protein under a promoter that is active in the embryo or seed, which makes the plant sterile where the gene promoter is under the control of a specific operator sequence responsive to activation by an activator protein.

2. An activator protein, whose gene is under the control of a constitutive promoter. Upon specific chemical binding to this activator it becomes non-active and can no longer activate the transcription of the first plasmid.

According to an exemplary embodiment, the disrupter gene used under the control of an upstream TRE followed by an embryogenesis, seed development or seed germination promoter is RIP (ribosomal inhibitor protein, sequence of a complete RIP gene, saporin 6:GenBank ID SOSAP6, Accession No. X15655) or barnase (Genbank Accession M14442). The tTA Gene is under a constitutive promoter. Upon application of tetracycline or its derivatives such as doxycycline the tTA becomes inactivated and results in inhibition of expression of the disrupter induced gene.

It will be appreciated that in the reverse process the disrupter gene is active however upon application of an inducer, the disrupter gene is turned off allowing the plant to survive and reproduce.

Thus, as mentioned, the disrupter gene promoter is under the control of a specific operator sequence. A further repressor protein, which gene is under control of a chemically or physically inducible promoter, can bind to the operator, inhibiting the expression of the disrupter protein. In the absence of the exogenous chemical inducer, no repressor protein is expressed; therefore, the breeder must apply the specific chemical inducer throughout the process of seed multiplication to inactivate the disrupter gene that causes sterility, terminating the application only at the time of selling the seeds.

A further technology contemplated herein refers to the recoverable block of function (RBF), which consists of a blocking sequence (e.g., encoding a barnase) linked to the gene of interest and a recovery sequence (e.g., encoding a barstar), expressed under control of sulfhydryl endopeptidase (SH-EP) and heat shock (HS) promoters, respectively, and all contained in a single insert. The natural expression of the barnase in embryos and sprouts confers cell death or prevents sexual reproduction (by blocking mRNA synthesis and germination) in the natural environment. The expression of the recovery sequence is induced by an artificial external stimulus such as a heat shock treatment or chemical application; recovery of the blocked function results in the 'restoration' of the viable/fertile phenotype.

Any seed formed from hybridization between wild weed and the GM pollen that contain the RBF will be unable to germinate because of the action of the blocking sequence. It will be appreciated that in sharp contrast to prior art methods, the genetically modified pollen with the RBF system that is used in the artificial pollination and is aimed at weed control does not have a gene of interest coupled to it. Alternatively, or additionally the plant can be transformed with any gene that results in reduced fitness (destruction gene) which expression can be induced.

Various inducible systems are known in the art. These include, but are not limited to, AlcR based ethanol inducible system, Tetracycline system, steroid-inducible systems such as but not limited to Glucocorticoid receptor-based, Dexamethasone-inducible, Estradiol inducible or Estrogen receptor-based, insecticide inducible systems such as but not limited to Ecdysone receptor-based, or ACEI-based, copper-inducible system. Additional inducible systems are Benzothiadiazole-inducible and Safener-inducible, Tebufenozide inducible or, Methoxyfenozide inducible systems [Padidam et al., 2003].

In the same manner the following constructs can be prepared, provided they are under an inducible regulation. Thus, transgenic weeds expressing EtoH inducible death gene are being produced using insertion of a plasmid encoding for AlcR based EtoH inducible promoter linked to a barnase gene or a RIP gene or transgenic plants expressing EtOH inducible EPSPS anti sense RNA to reduce EPSPS levels upon ethanol application.

Examples of genes that can be modulated in order to reduce tolerance to biotic or abiotic stress include, but are not limited to, HSF, MYB, MYC, AP2/ERF, NAC, ZF, HSP, MAPK, LEA, SOS or CYP (Atkinson N J and Urwin P E, 2012); or microRNA families such as MIR156, MIR166, MIR167, MIR169 (Khraiwesh, B. et al., 2012).

Another option is generating a weed strain that produces pollen that is genetically modified to express an inhibitor of a gene that is responsible for herbicide resistance or tolerance (e.g., biotic or abiotic) such as a silencing agent or DNA editing agent (e.g., CRISPR-Cas9, as further detailed below) that modulates expression of a target molecule e.g., herbicide targeted molecule such as but not limited to genes related to ACCase, ALS, Photosystem II, PSI Electron Diverter, PPO, Carotenoid biosynthesis, HPPD, EPSP synthase, Glutamine synthase, DHP synthase, Mitosis, Auxin transport, Uncouplers, Antimicrotubule mitotic disrupter, Cell elongation or in the process of generation of Microtubule, Long chain fatty acid, Cellulose, Lipid, Nucleic acid or modulating expression of any other critical gene participating in the fertilization process, embryonic development, seed development or germination process.

Examples of platform technologies that can be used to down-regulate gene expression include, but are not limited to downregulation (gene silencing) of the transcription or translation product of an endogenous gene can be achieved by co-suppression, antisense suppression, RNA interference and ribozyme molecules.

Co-suppression (sense suppression)—Inhibition of the endogenous gene can be achieved by co-suppression, using an RNA molecule (or an expression vector encoding same) which is in the sense orientation with respect to the transcription direction of the endogenous gene. The polynucleotide used for co-suppression may correspond to all or part of the sequence encoding the endogenous polypeptide and/or to all or part of the 5' and/or 3' untranslated region of the endogenous transcript; it may also be an unpolyadenylated RNA; an RNA which lacks a 5' cap structure; or an RNA which contains an unsplicable intron.

In some embodiments, the polynucleotide used for co-suppression is designed to eliminate the start codon of the endogenous polynucleotide so that no protein product will be translated. Methods of co-suppression using a full-length cDNA sequence as well as a partial cDNA sequence are known in the art (see, for example, U.S. Pat. No. 5,231,020).

According to some embodiments of the invention, down-regulation of the endogenous gene is performed using an amplicon expression vector which comprises a plant virus-derived sequence that contains all or part of the target gene but generally not all of the genes of the native virus. The viral sequences present in the transcription product of the expression vector allow the transcription product to direct its own replication. The transcripts produced by the amplicon may be either sense or antisense relative to the target sequence [see for example, Angell and Baulcombe, (1997) *EMBO J.* 16:3675-3684; Angell and Baulcombe, (1999) *Plant J.* 20:357-362, and U.S. Pat. No. 6,646,805, each of which is herein incorporated by reference].

Antisense suppression—Antisense suppression can be performed using an antisense polynucleotide or an expression vector which is designed to express an RNA molecule complementary to all or part of the messenger RNA (mRNA) encoding the endogenous polypeptide and/or to all or part of the 5' and/or 3' untranslated region of the endogenous gene. Over expression of the antisense RNA molecule can result in reduced expression of the native (endogenous) gene. The antisense polynucleotide may be fully complementary to the target sequence (i.e., 100% identical to the complement of the target sequence) or partially complementary to the target sequence (i.e., less than 100% identical, e.g., less than 90%, less than 80% identical to the complement of the target sequence).

Antisense suppression may be used to inhibit the expression of multiple proteins in the same plant (see e.g., U.S. Pat. No. 5,942,657). In addition, portions of the antisense nucleotides may be used to disrupt the expression of the target gene. Generally, sequences of at least about 50 nucleotides, at least about 100 nucleotides, at least about 200 nucleotides, at least about 300, at least about 400, at least about 450, at least about 500, at least about 550, or greater may be used. Methods of using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference.

Efficiency of antisense suppression may be increased by including a poly-dT region in the expression cassette at a position 3' to the antisense sequence and 5' of the polyadenylation signal [See, U.S. Patent Publication No. 20020048814, herein incorporated by reference].

RNA interference—RNA interference can be achieved using a polynucleotide, which can anneal to itself and form a double stranded RNA having a stem-loop structure (also called hairpin structure), or using two polynucleotides, which form a double stranded RNA.

For hairpin RNA (hpRNA) interference, the expression vector is designed to express an RNA molecule that hybridizes to itself to form a hairpin structure that comprises a single-stranded loop region and a base-paired stem.

In some embodiments of the invention, the base-paired stem region of the hpRNA molecule determines the specificity of the RNA interference. In this configuration, the sense sequence of the base-paired stem region may correspond to all or part of the endogenous mRNA to be downregulated, or to a portion of a promoter sequence controlling expression of the endogenous gene to be inhibited; and the antisense sequence of the base-paired stem region is fully or partially complementary to the sense sequence. Such hpRNA molecules are highly efficient at inhibiting the expression of endogenous genes, in a manner which is inherited by subsequent generations of plants [See, e.g., Chuang and Meyerowitz, (2000) Proc. Natl. Acad. Sci. USA 97:4985-4990; Stoutjesdijk, et al., (2002) Plant Physiol. 129:1723-1731; and Waterhouse and Helliwell, (2003) Nat. Rev. Genet. 4:29-38; Chuang and Meyerowitz, (2000) Proc. Natl. Acad. Sci. USA 97:4985-4990; Pandolfini et al., BMC Biotechnology 3:7; Panstruga, et al., (2003) Mol. Biol. Rep. 30:135-140; and U.S. Patent Publication No. 2003/0175965; each of which is incorporated by reference].

According to some embodiments of the invention, the sense sequence of the base-paired stem is from about 10 nucleotides to about 2,500 nucleotides in length, e.g., from about 10 nucleotides to about 500 nucleotides, e.g., from about 15 nucleotides to about 300 nucleotides, e.g., from about 20 nucleotides to about 100 nucleotides, e.g., or from about 25 nucleotides to about 100 nucleotides.

According to some embodiments of the invention, the antisense sequence of the base-paired stem may have a length that is shorter, the same as, or longer than the length of the corresponding sense sequence.

According to some embodiments of the invention, the loop portion of the hpRNA can be from about 10 nucleotides to about 500 nucleotides in length, for example from about 15 nucleotides to about 100 nucleotides, from about 20 nucleotides to about 300 nucleotides or from about 25 nucleotides to about 400 nucleotides in length.

According to some embodiments of the invention, the loop portion of the hpRNA can include an intron (ihpRNA), which is capable of being spliced in the host cell. The use of an intron minimizes the size of the loop in the hairpin RNA molecule following splicing and thus increases efficiency of the interference [See, for example, Smith, et al., (2000) Nature 407:319-320; Wesley, et al., (2001) Plant J. 27:581-590; Wang and Waterhouse, (2001) Curr. Opin. Plant Biol. 5:146-150; Helliwell and Waterhouse, (2003) Methods 30:289-295; Brummell, et al. (2003) Plant J. 33:793-800; and U.S. Patent Publication No. 2003/0180945; WO 98/53083; WO 99/32619; WO 98/36083; WO 99/53050; US 20040214330; US 20030180945; U.S. Pat. Nos. 5,034,323; 6,452,067; 6,777,588; 6,573,099 and 6,326,527; each of which is herein incorporated by reference].

In some embodiments of the invention, the loop region of the hairpin RNA determines the specificity of the RNA interference to its target endogenous RNA. In this configuration, the loop sequence corresponds to all or part of the endogenous messenger RNA of the target gene. See, for example, WO 02/00904; Mette, et al., (2000) EMBO J 19:5194-5201; Matzke, et al., (2001) Curr. Opin. Genet. Devel. 11:221-227; Scheid, et al., (2002) Proc. Natl. Acad. Sci., USA 99:13659-13662; Aufsaftz, et al., (2002) Proc. Nat'l. Acad. Sci. 99(4):16499-16506; Sijen, et al., Curr. Biol. (2001) 11:436-440), each of which is incorporated herein by reference. For double-stranded RNA (dsRNA) interference, the sense and antisense RNA molecules can be expressed in the same cell from a single expression vector (which comprises sequences of both strands) or from two expression vectors (each comprising the sequence of one of the strands). Methods for using dsRNA interference to inhibit the expression of endogenous plant genes are described in Waterhouse, et al., (1998) Proc. Natl. Acad. Sci. USA 95:13959-13964; and WO 99/49029, WO 99/53050, WO 99/61631, and WO 00/49035; each of which is herein incorporated by reference.

According to some embodiments of the invention, RNA interference is effected using an expression vector designed to express an RNA molecule that is modeled on an endogenous micro RNAs (miRNA) gene. Micro RNAs (miRNAs) are regulatory agents consisting of about 22 ribonucleotides and highly efficient at inhibiting the expression of endogenous genes [Javier, et al., (2003) Nature 425:257-263]. The miRNA gene encodes an RNA that forms a hairpin structure containing a 22-nucleotide sequence that is complementary to the endogenous target gene.

Ribozyme—Catalytic RNA molecules, ribozymes, are designed to cleave particular mRNA transcripts, thus preventing expression of their encoded polypeptides. Ribozymes cleave mRNA at site-specific recognition sequences. For example, "hammerhead ribozymes" (see, for example, U.S. Pat. No. 5,254,678) cleave mRNAs at locations dictated by flanking regions that form complementary base pairs with the target mRNA. The sole requirement is that the target RNA contains a 5'-UG-3' nucleotide sequence. Hammerhead ribozyme sequences can be embedded in a stable RNA such as a transfer RNA (tRNA) to increase cleavage efficiency in vivo [Perriman et al. (1995) Proc. Natl. Acad. Sci. USA, 92(13):6175-6179; de Feyter and Gaudron Methods in Molecular Biology, Vol. 74, Chapter 43, "Expressing Ribozymes in Plants", Edited by Turner, P. C, Humana Press Inc., Totowa, N.J.; U.S. Pat. No. 6,423,885]. RNA endoribonucleases such as that found in *Tetrahymena thermophila* are also useful ribozymes (U.S. Pat. No. 4,987,071).

Constructs useful in the methods according to some embodiments of the invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of promoters useful for the methods of some embodiments of the invention are presented in Table 1.

TABLE 1

Exemplary constitutive promoters for use in the performance of some embodiments of the invention

| Gene Source | Expression Pattern | Reference |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |

According to some embodiments of the invention, overexpression is achieved by means of genome editing. However, the same means can be used to down-regulate gene expression all dependent on the design of the gene editing tool.

Genome editing is a reverse genetics method which uses artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location.

To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Over expression of a polypeptide by genome editing can be achieved by: (i) replacing an endogenous sequence encoding the polypeptide of interest, and/or (ii) inserting a new gene encoding the polypeptide of interest in a targeted region of the genome, and/or (iii) introducing point mutations which result in up-regulation of the gene encoding the polypeptide of interest (e.g., by altering the regulatory sequences such as promoter, enhancers, 5'-UTR and/or 3'-UTR). Downregulation of a gene of interest can be achieved by introducing point mutations which result in down-regulation of the gene encoding the polypeptide of interest (e.g., by altering the regulatory sequences such as promoter, enhancers, 5'-UTR and/or 3'-UTR, inserting mutations in a catalytic site or protein-protein interaction interface).

Homology Directed Repair (HDR).

Homology Directed Repair (HDR) can be used to generate specific nucleotide changes (also known as gene "edits") ranging from a single nucleotide change to large insertions. In order to utilize HDR for gene editing, a DNA "repair template" containing the desired sequence must be delivered into the cell type of interest with the guide RNA [gRNA(s)] and Cas9 or Cas9 nickase. The repair template must contain the desired edit as well as additional homologous sequence immediately upstream and downstream of the target (termed left and right homology arms). The length and binding position of each homology arm is dependent on the size of the change being introduced. The repair template can be a single stranded oligonucleotide, double-stranded oligonucleotide, or double-stranded DNA plasmid depending on the specific application. It is worth noting that the repair template must lack the Protospacer Adjacent Motif (PAM) sequence that is present in the genomic DNA, otherwise the repair template becomes a suitable target for Cas9 cleavage. For example, the PAM could be mutated such that it is no longer present, but the coding region of the gene is not affected (i.e. a silent mutation).

The efficiency of HDR is generally low (<10% of modified alleles) even in cells that express Cas9, gRNA and an exogenous repair template.

For this reason, many laboratories are attempting to artificially enhance HDR by synchronizing the cells within the cell cycle stage when HDR is most active, or by chemically or genetically inhibiting genes involved in Non-Homologous End Joining (NHEJ). The low efficiency of HDR has several important practical implications. First, since the efficiency of Cas9 cleavage is relatively high and the efficiency of HDR is relatively low, a portion of the Cas9-induced double strand breaks (DSBs) will be repaired via NHEJ. In other words, the resulting population of cells will contain some combination of wild-type alleles, NHEJ-repaired alleles, and/or the desired HDR-edited allele.

Therefore, it is important to confirm the presence of the desired edit experimentally, and if necessary, isolate clones containing the desired edit.

The HDR method was successfully used for targeting a specific modification in a coding sequence of a gene in plants (Budhagatapalli Nagaveni et al. 2015. "Targeted Modification of Gene Function Exploiting Homology-Directed Repair of TALEN-Mediated Double-Strand Breaks in Barley". G3 (Bethesda). 2015 September; 5(9): 1857-1863). Thus, the gfp-specific transcription activator-like effector nucleases were used along with a repair template that, via HDR, facilitates conversion of gfp into yfp, which is associated with a single amino acid exchange in the gene product. The resulting yellow-fluorescent protein accumulation along with sequencing confirmed the success of the genomic editing.

Similarly, Zhao Yongping et al. 2016 (An alternative strategy for targeted gene replacement in plants using a dual-sgRNA/Cas9 design. Scientific Reports 6, Article number: 23890 (2016)) describe co-transformation of *Arabidopsis* plants with a combinatory dual-sgRNA/Cas9 vector that successfully deleted miRNA gene regions (MIR169a and MIR827a) and second construct that contains sites homologous to *Arabidopsis* TERMINAL FLOWER 1 (TFL1) for homology-directed repair (HDR) with regions corresponding to the two sgRNAs on the modified construct to provide both targeted deletion and donor repair for targeted gene replacement by HDR.

Activation of Target Genes Using CRISPR/Cas9.

Many bacteria and archaea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components.

The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of CRISPR-associated endonuclease (Cas9) in conjunction with synthetic gRNAs can be used to produce targeted double-stranded brakes in a variety of different species.

The CRISPR/Cas9 system is a remarkably flexible tool for genome manipulation. A unique feature of Cas9 is its ability to bind target DNA independently of its ability to cleave target DNA. Specifically, both RuvC- and HNH-nuclease domains can be rendered inactive by point mutations (D10A and H840A in SpCas9), resulting in a nuclease dead Cas9 (dCas9) molecule that cannot cleave target DNA. The dCas9 molecule retains the ability to bind to target DNA based on the gRNA targeting sequence. The dCas9 can be tagged with transcriptional activators, and targeting these dCas9 fusion proteins to the promoter region results in robust transcription activation of downstream target genes. The simplest dCas9-based activators consist of dCas9 fused directly to a single transcriptional activator.

Importantly, unlike the genome modifications induced by Cas9 or Cas9 nickase, dCas9-mediated gene activation is reversible, since it does not permanently modify the genomic DNA.

Indeed, genome editing was successfully used to overexpress a protein of interest in a plant by, for example, mutating a regulatory sequence, such as a promoter to overexpress the endogenous polynucleotide operably linked to the regulatory sequence. For example, U.S. Patent Application Publication No. 20160102316 to Rubio Munoz, Vicente et al. which is fully incorporated herein by reference, describes plants with increased expression of an endogenous DDA1 plant nucleic acid sequence wherein the endogenous DDA1 promoter carries a mutation introduced by mutagenesis or genome editing which results in increased expression of the DDA1 gene, using for example, CRISPR. The method involves targeting of Cas9 to the specific genomic locus, in this case DDA1, via a 20 nucleotide guide sequence of the single-guide RNA. An online CRISPR Design Tool can identify suitable target sites (www(dot)tools(dot)genome-engineering(dot)org. Ran et al. Genome engineering using the CRISPR-Cas9 system nature protocols, VOL. 8 NO. 11, 2281-2308, 2013).

The CRISPR-Cas system was used for altering gene expression in plants as described in U.S. Patent Application publication No. 20150067922 to Yang; Yinong et al., which is fully incorporated herein by reference. Thus, the engineered, non-naturally occurring gene editing system comprises two regulatory elements, wherein the first regulatory element (a) operable in a plant cell operably linked to at least one nucleotide sequence encoding a CRISPR-Cas system guide RNA (gRNA) that hybridizes with the target sequence in the plant, and a second regulatory element (b) operable in a plant cell operably linked to a nucleotide sequence encoding a Type-II CRISPR-associated nuclease, wherein components (a) and (b) are located on same or different vectors of the system, whereby the guide RNA targets the target sequence and the CRISPR-associated nuclease cleaves the DNA molecule, thus altering the expression of a gene product in a plant. It should be noted that the CRISPR-associated nuclease and the guide RNA do not naturally occur together.

In addition, as described above, point mutations which activate a gene-of-interest and/or which result in overexpression of a polypeptide-of-interest can be also introduced into plants by means of genome editing. Such mutation can be for example, deletions of repressor sequences which result in activation of the gene-of-interest; and/or mutations which insert nucleotides and result in activation of regulatory sequences such as promoters and/or enhancers.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity.

Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8, 148,098; or 8, 163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI.

Additionally FokI has the advantage of requiring dimerization to have nuclease activity and this means the specificity increases dramatically as each nuclease partner recognizes a unique DNA sequence.

To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break.

Repair of these double-stranded breaks through the non-homologous end-joining (NHEJ) pathway most often results in small deletions or small sequence insertions. Since each repair made by NHEJ is unique, the use of a single nuclease pair can produce an allelic series with a range of different deletions at the target site.

The deletions typically range anywhere from a few base pairs to a few hundred base pairs in length, but larger deletions have successfully been generated in cell culture by using two pairs of nucleases simultaneously (Carlson et al., 2012; Lee et al., 2010).

In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs.

Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, Calif.).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type.

The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRY", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats.

Cre recombines the 34 base pair lox DNA sequence by binding to the 13 base pair inverted repeats and catalyzing strand cleavage and relegation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, 2003 31(23): 6873-6881].

Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred.

The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified.

Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells.

The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

Thus, according to some embodiments of the invention the pollen of the invention confers reduced fitness by way of partial genome incompatibility, parthenocarpy, stenospermocarpy, reduced shattering, inhibition of seed dormancy, cleistogamy, induced triploidy, conditional lethality, male sterility, female sterility, inducible promoters, complete sterility by nonflowering, reduced biotic/abiotic stress tolerance. The skilled artisan will know which method to select.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA.

Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant.

Micropropagation allows mass production of quality plant material in a short period of time and offers a rapid multiplication of selected cultivars in the preservation of the characteristics of the original transgenic or transformed plant.

The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced from the seedlings to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus.

Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Taylor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters.

Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, N.Y.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide.

Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Specific methods for weed transformation are described in Jofre-Garfias et al., 1997, Swain et al., 2010 and Pal et al., 2013, each of which is incorporated by reference in its entirety. According to a further aspect of the invention there is provided a method of producing pollen, the method comprising:

(a) growing weed producing pollen that reduces fitness of at least one weed species of interest; and (b) harvesting the pollen.

Thus the pollen product producing weed is grown in dedicated settings, e.g., open or closed settings, e.g., a greenhouse. According to a specific embodiment, the growth environment for the manufacture of the pollen does not include crop plants or the weed species of interest. For example, the growth area includes an herbicide susceptible weed variant but not a herbicide resistant weed variant (of the same species). Another example, the growth environment comprises a GM weed with a destructor gene the weed being fertile and producing pollen, but doesn't include the weed in which the destructor gene is expressed.

According to a specific embodiment, growing the weed producing pollen that reduces fitness is effected in a large scale setting (e.g., hundreds to thousands $m^2$).

According to some embodiments of the invention, the weed producing pollen comprises only male plants.

Harvesting pollen is well known in the art. For example, by the use of paper bags. Another example is taught in U.S. 20060053686, which is hereby incorporated by reference in its entirety.

Once pollen is obtained it can be stored for future use. Examples of storage conditions include, but are not; limited to, storage temperatures in Celsius degrees e.g., −196, −160, −130, −80, −20, −5, 0, 4, 20, 25, 30 or 35; percent of relative humidity e.g., 0, 10, 20, 30, 40, 50, 60, 70, 80, 90 or 100. Control over humidity can be achieved by using a dehydrating agent as known in the art. Additionally, the pollen can be stored in light or dark.

Alternatively, the pollen product of the present teachings is subjected to a post harvest treatment.

Thus, according to an aspect of the invention there is provided a method of producing pollen for use in artificial pollination, the method comprising:

(a) obtaining pollen that reduces fitness of at least one weed species of interest, e.g., as described herein; and (b) treating the pollen for use in artificial pollination.

Accordingly, there is provided a composition of matter comprising weed pollen that reduces fitness of at least one weed species of interest, the pollen having been treated for improving its use in artificial pollination.

Examples of such treatments include, but are not limited to coating, priming, formulating, chemical inducers, physical inducers [e.g., potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide], solvent solubilization, drying, heating, cooling and irradiating (e.g., gamma, UV, X-ray, particle).

Additional ingredients and additives can be advantageously added to the pollen composition of the present invention and may further contain sugar, potassium, calcium, boron, and nitrates. These additives may promote pollen tube growth after pollen distribution on flowering plants.

In some embodiments, the pollen composition of the present invention contains dehydrated or partially dehydrated pollen.

Thus, the pollen composition may comprise a surfactant, a stabilizer, a buffer, a preservative, an antioxidant, an extender, a solvent, an emulsifier, an invert emulsifier, a spreader, a sticker, a penetrant, a foaming agent, an antifoaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, a herbicide or a pesticide.

Other ingredients and further description of the above ingredients is provided hereinbelow.

Under ordinary conditions of storage and use, the composition of the present invention may contain a preservative to prevent the growth of microorganisms.

The preventions of the action of microorganisms can be brought about by various antibacterial and antifungal agents, for example, parabens, chlorobutanol, sorbic acid, and the like. Antioxidants may also be added to the pollen suspension to preserve the pollen from oxidative damage during storage. Suitable antioxidants include, for example, ascorbic acid, tocopherol, sulfites, metabisulfites such as potassium metabisulfite, butylhydroxytoluene, and butylhydroxyanisole.

Thus, pollen compositions that may also be used but not limited to mixtures with various agricultural chemicals and/or herbicides, insecticides, miticides and fungicides, pesticidal and biopesticidal agents, nematocides, bactericides, acaricides, growth regulators, chemosterilants, semiochemicals, repellents, attractants, pheromones, feeding stimulants or other biologically active compounds all of which can be added to the pollen to form a multi-component composition giving an even broader spectrum of agricultural protection.

Thus in the artificial pollination method of the present invention can be applied together with the following herbicides but not limited to: ALS inhibitor herbicide, auxin-like herbicides, glyphosate, glufosinate, sulfonylureas, imidazolinones, bromoxynil, delapon, dicamba, cyclohezanedione, protoporphyrionogen oxidase inhibitors, 4-hydroxyphenyl-pyruvate-dioxygenase inhibitors herbicides.

In some embodiments, the pollen can be combined with appropriate solvents or surfactants to form a formulation. Formulations enable the uniform distribution of a relatively small amount of the pollen over a comparatively large growth area. In addition to providing the user with a form of a pollen that is easy to handle, formulating can enhance its fertilization activity, improve its ability to be applied to a plant, enable the combination of aqueous-soluble and organic-soluble compounds, improve its shelf-life, and protect it from adverse environmental conditions while in storage or transit.

Numerous formulations are known in the art and include, but are not limited to, solutions, soluble powders, emulsifiable concentrates, wettable powders, liquid flowables, and dry flowables. Formulations vary according to the solubility of the active or additional formulation ingredients in water, oil and organic solvents, and the manner the formulation is applied (i.e., dispersed in a carrier, such as water, or applied as a dry formulation).

Hence, contemplated are wet (e.g., liquid) as well as dry formulations.

Solution formulations are designed for those active ingredients that dissolve readily in water or other non-organic solvents such as methanol. The formulation is a liquid and comprises of the active ingredient and additives.

Suitable liquid carriers, such as solvents, may be organic or inorganic. Water is one example of an inorganic liquid carrier. Organic liquid carriers include vegetable oils and epoxidized vegetable oils, such as rape seed oil, castor oil, coconut oil, soybean oil and epoxidized rape seed oil, epoxidized castor oil, epoxidized coconut oil, epoxidized soybean oil, and other essential oils. Other organic liquid carriers include aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Soluble powder formulations are similar to solutions in that, when mixed with water, they dissolve readily and form a true solution. Soluble powder formulations are dry and include the active ingredient and additives.

Emulsifiable concentrate formulations are liquids that contain the active ingredient, one or more solvents, and an emulsifier that allows mixing with a component in an organic liquid carrier. Formulations of this type are highly concentrated, relatively inexpensive per pound of active ingredient, and easy to handle, transport, and store. In addition, they require little agitation (will not settle out or separate) and are not abrasive to machinery or spraying equipment.

Wettable powders are dry, finely ground formulations in which the active ingredient is combined with a finely ground carrier (usually mineral clay), along with other ingredients to enhance the ability of the powder to suspend in water. Generally, the powder is mixed with water for application. Typical solid diluents are described in Watkins et al., Handbook of Insecticide Dust Diluents and Carriers, 2nd Ed., Dorland Books, Caldwell, N.J. The more absorptive diluents are preferred for wettable powders and the denser ones for dusts.

Liquid flowable formulations are made up of finely ground active ingredient suspended in a liquid. Dry flowable and water-dispersible granule formulations are much like wettable powders except that the active ingredient is formulated on a large particle (granule) instead of onto a ground powder.

The methods of making such formulations are well known. Solutions are prepared by simply mixing the ingredients. Fine, solid compositions are made by blending and, usually, grinding, as in a hammer or fluid energy mill. Suspensions are prepared by wet-milling (see, for example, U.S. Pat. No. 3,060,084).

The concentration of a pollen growth stimulating compound in a formulation may vary according to particular compositions and applications.

In some embodiments of the disclosure, inactive ingredients i.e., adjuvants) are added to pollen to improve the performance of the formulation. For example, in one embodiment of the disclosure, pollen is formulated with a surfactant. A surfactant (surface active agent) is a type of adjuvant formulated to improve the dispersing/emulsifying, absorbing, spreading, and sticking properties of a spray mixture. Surfactants can be divided into the following five groupings: (1) non-ionic surfactants, (2) crop oil concentrates, (3) nitrogen-surfactant blends, (4) esterified seed oils, and (5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical.

The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis(2-chloroethyl)ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Other adjuvants include carriers and additives, for example, wetting agents, such as anionic, cationic, nonionic, and amphoteric surfactants, buffers, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, antibiotics, fungicides, nematicides, or pesticides (others are described hereinabove). Such carriers and additives may be used in solid, liquid, gas, or gel form, depending on the embodiment and its intended application.

As used herein "artificial pollination" is the application, by hand, insects (e.g., bees) or dedicated machinery, of fertile stigmas with the pollen from plants with desired characteristics, as described herein.

Artificial pollination in the field can be achieved by pollen spraying (e.g., wet or dry spray formulations), spreading, dispersing or any other method. The application itself will be performed by ground equipment, aircraft, unmanned aerial vehicles (UAV), remote-piloted vehicles(RPV), drones or specialized robots, special vehicles or tractors, animal assisted, specialized apparatus that is designed to spread boosts of pollen, specialized apparatus that combines ventilation and spraying of pollen to enhance recycling of pollen or any other application method or apparatus wherein application can be of a single dose, multiple doses, continuous, on an hourly/daily/weekly/monthly basis or any other application timing methodology.

It will be appreciated that pollination of female flowers is necessary.

According to a specific embodiment, the whole growth area is pollinated at flowering.

According to another specific embodiment, only female flowers are pollinated while male flowers are either left untreated or treated using other means, e.g., herbicides, harvesting etc.

It will be appreciated that at any time the weed of interest can be further treated with other weed control means. For example, the weed may be treated with a herbicide (which is usually applied at early stages of germination as opposed to the pollen which is applied at flowering). Thus a herbicide for instance can be applied prior to, concomitantly with or following pollen treatment.

Any of the pollen compositions described herein can be produced as a single species pollen with a single trait for reducing weed fitness, a single species pollen with a plurality of traits for reducing weed fitness (e.g., a number of different herbicide resistances or a number of sterility encoding mechanisms) all introduced into a single weed or to a plurality of weeds of the same species, a multispecies pollen with a single trait or a multispecies pollen with a plurality of said traits.

Thus, commercial products can be manufactured as kits whereby each pollen type is packed in a separate packaging means (e.g., bag), or two or more types of pollen are combined into a single composition and packed in a single packaging means (e.g., bag). The product may be accompanied by instructions for use, regulatory information, product description and the like.

The kit may also include in a separate packaging means other active ingredients such as at least one of a chemical inducer (as described above), herbicide, fertilizer, antibiotics and the like.

Reference is now made to FIG. 1, which is a flowchart of a method for reducing fitness of at least one weed species of interest, in accordance with some embodiments of the present invention. Reference is also made to FIG. 2, which is a flowchart of a method of training one or more statistical classifiers for reducing fitness of at least one weed species of interest, in accordance with some embodiments of the present invention. Reference is also made to FIG. 3, which is a block diagram of components of a system 300 for providing a pollination controller 302 of a pollinating device 304 with instructions for artificially pollinating flowers of the at least one weed species of interest with pollen that reduces fitness of the at least one weed species of interest, and/or for training one or more statistical classifiers 306 for reducing fertilization of weeds in a field, in accordance with some embodiments of the present invention. System 300 may implement the acts of the methods described with reference to FIGS. 1-2, optionally by a hardware processor(s) 308 of a computing device 310 executing code instructions 312A and/or training code 312B stored in a memory 312.

Pollinator device 304 may be mobile and/or stationary.

Pollinator device 304 may be coupled to and/or integrated with one or more machinery 314, for example, a ground based machinery (e.g., land vehicle such as tractor), and/or an aerial based machinery (e.g., plane, drone).

Pollinator device 304 may include a sprayer located at a predefined height above the ground, and/or above crops growing in a field where the weed species of interest is/are growing and/or static puffer placed on the ground.

Pollinator device 304 may be installed in a stationary and/or fixed state, for example, an architecture of tubes running throughout the field attached to fixed sprayers.

Pollinator device 304 may include a mechanism to attract bees, and for coupling the pollen to the bees for administration to the flower of the at least one weed species of interest. Alternatively or additionally, the bees are inside a hive and when going out are taking pollen with them to apply on flowers. The pollen may be applied to the bees by the pollinator device. Exemplary machinery 314, such as ground based and/or aerial based machinery, is as described herein, and may include, for example, a tractor, a jeep, a 4×4 vehicle, a car, a truck, an unmanned aerial vehicle (UAV), a remote-piloted vehicle (RPV), a satellite, a surveillance aircraft, a drone, a specialized robot, a robot bee, a robobee, and a robo-bee.

Is it noted that one or two or more machinery 314 may be implemented, for example, the same machinery type (or the same machine itself) may include the sensor and the pollinator device to perform the imaging and the pollination (e.g., aerial imaging and pollination, or ground based imaging and pollination), or different machinery may respectively include the sensor and the pollinator, for example, aerial imaging and ground based pollination, or ground based imaging and aerial pollination. The imaging and pollination may occur approximately simultaneously, or separated by a time interval, as described herein.

Alternatively or additionally geographical location sensor(s) 316 and/or imaging sensor(s) 326 are coupled and/or integrated with one or more machinery 314 and/or coupled and/or integrated with pollinator device 304 and/or pollination controller 302, for example, for associating captured images with location data, and/or for controlling the pollinator device 304 to pollinate a certain location according to the location data.

Geographical location sensor(s) 316 output a location of the scene represented within the captured image(s) and/or the location of the machinery. Exemplary location sensor(s) 316 include, for example, a global positioning system (GPS) device, an a trackable cellular phone (e.g., smartphone) where the location of the phone may be computed for example, by triangulation of cellular signals.

Pollinator controller 302 may be integrated with pollinator device 304, for example, as a hardware processor(s) and/or computing device. Pollinator controller 302 may be in remote communication with pollinator device 304, for example, over a wireless and/or wired network, for example, a land base computer in communication with a transmitter that transmits to aerial machinery 314 that houses pollinator device 304 (e.g., land base computer that transmits to an unmanned machinery that includes a sprayer).

System 300 may include code instructions 312B for training classifier(s) 306. Training code 312B may be stored in memory 312 and/or a data storage device 318. Alternatively, classifier(s) 306 is trained by another computing device (e.g., server 320) and transmitted to computing device 310 over a network 322 and/or remotely accessed by computing device 310 over network 322 (e.g., via a software interface for example, application programming interface (API), and/or software development kit (SDK)).

Multiple architectures of system 300 based on computing device 310 may be implemented. For example, computing device 310 may be integrated with pollinator device 304, for example, code 312A is stored on a memory of pollinator device 304 for execution by pollinator controller 302. In another implementation, computing device 310 may be implemented as a dedicated device in communication with pollinator device 304 and/or pollinator controller 302, for example, via a cable, a connector slot, a short range network, and/or network 322. In another exemplary implementation, computing device 310 may be implemented as one or more servers (e.g., network server, web server, a computing cloud, a virtual server) that provides remote services to one or more pollinator devices 304 and/or pollinator controllers 302 over network 322, and/or to remote client terminals 324 where each client terminal 324 is locally in communication with and/or is integrated with a respective pollinator device and/or pollinator controller.

In yet another implementation, the classifier is executed by computing device 310, and the instructions are locally generated by respective client terminals 324 that access a server implementation of computing device 310. In this manner, the classifier centrally computes the indication (as described herein), and each respective client terminal 324 may locally generate its own set of instructions for its own associated pollinator device 304 and/or pollinator controller 302, for example, according to local environmental conditions and/or local pollinator hardware.

Computing device 310 may be implemented as, for example, code executing on pollinator controller 302, a client terminal, a server, a computing cloud, a virtual machine, a virtual server, a mobile device, a desktop computer, a thin client, a Smartphone, a Tablet computer, a laptop computer, a wearable computer, glasses computer, and a watch computer.

Computing device 310 is in communication with one or more imaging sensor(s) 326 that capture image(s) that include the weed species of interest. The imaging sensor(s) 326 may output 2D and/or 3D images. The imaging sensor(s) may include a still camera and/or video camera. Exemplary imaging sensor(s) 326 include: a reflectance sensor that captures light applied by a light source reflected from the at least one weed species of interest, a spectral image sensor, multispectral image sensor, hyperspectral image sensor, and a visible light sensor The imaging sensor(s) 326 may be fixed in place (e.g., cameras that monitor the field), and/or may be mobile (e.g., connected to land based and/or aerial vehicles).

Hardware processor(s) 308 may be implemented, for example, as a central processing unit(s) (CPU), a graphics processing unit(s) (GPU), field programmable gate array(s) (FPGA), digital signal processor(s) (DSP), and/or application specific integrated circuit(s) (ASIC). Processor(s) 308 may include one or more processors (homogenous or heterogeneous), which may be arranged for parallel processing, as clusters and/or as one or more multi core processors.

Memory 312 stores code instructions 312A and/or 312B executable by processor(s) 308. Memory 312 may be implemented as, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Optionally, computing device 310 includes and/or is in communication with a data storage device 318 for example, for storing classifier 306, and/or for storing received images in an image repository 318A. Data storage device 318 may be implemented as, for example, a memory, a local harddrive, a removable storage device, an optical disk, a storage device, and/or as a remote server and/or computing cloud (e.g., accessed using a network connection). It is noted that code stored in data storage device 318 may be loaded into memory 312 for execution by processor(s) 308.

Optionally, computing device 310 is in communication with a user interface 328. User interface 328 may include a mechanism for the user to enter data (e.g., select the desired species of weed) and/or view data (e.g., the generated instructions), for example, a touch screen, a display, a mouse, a keyboard, and/or a microphone with voice recognition software. User interface 328 may include a graphical user interface (GUI) presented on a display.

Network 322 may be implemented as, for example, the internet, a local area network, a virtual network, a wireless network, a cellular network, a local bus, a point to point link (e.g., wired), and/or combinations of the aforementioned.

Referring now back to FIG. 1, at 102, one or more classifiers are provided. The classifier(s) are trained on a training dataset that includes multiples of images, each image storing one or more weeds of one or more species of interest captured by imaging sensor(s). Each image is associated with an indication (e.g., tag, metadata) of a time interval of when the respective weed(s) species of interest is/are at the target growth state suitable for artificial pollination of flowers of the weeds relative to the time of capture of the respective image, for example, immediately, in 1 day, in 3 days, in 1 week, in 2 weeks, in 1 month, or other values.

The training dataset may include, in association with one or more of the images, respective instructions for execution by the pollination controller of the pollinator device for artificially pollinating flowers of the weed(s) species of interest with pollen that reduces fitness of the at least one weed species of interest.

The training data set may include, in association with one or more images, additional data (e.g., a supplemental data profile including multiple supplemental data parameters) indicative of the environment of the weed, for example, geographic location, date of the year, temperature, humidity, geological forecasts, altitude, soil type, density of weeds, wind speed, wind direction, previously applied anti-weed treatments. The supplemental data may include details of the pollination to be applied, and/or the hardware of the pollinator device, optionally in implementation in which the classifier computes the instructions for execution by the pollinator controller.

A single classifier may be trained on the training dataset to identify multiple different species of weeds. Alternatively or additionally, multiple classifiers are trained on the training dataset, where each classifier identifies one type of species of weed. In such a case, the user may select the one or more classifiers according to desired weeds species of interest.

The classifier may be trained to analyze an image with multiple instances of the same weed species. The classifier may be trained to analyze an image with multiple instances of different types of weed species. The classifier may be trained to analyze an image that is expected to include a single weed of a the desired species, and/or a single weed of unknown species, in which case, the image outputted by the image sensor may be set (e.g., sized, focused) to include an area large enough to include only one weed, or an image including multiple weeds may be divided into sub-regions (e.g., patches), where each region is sized to include only one weed, where each sub-region (e.g., patch) is analyzed by the classifier.

The classifier may be trained to analyze an image with one or more weeds including background (e.g., other plants, rocks, earth). The classifier may be trained to analyze images only of weeds (i.e., excluding background), in which case, the images may be pre-processed, for example, by executing segmentation code for segmenting the weed, and feeding the segmented weed to the classifier.

The classifier may include a single classifier, or multiple classifiers arranged into a unique architecture.

Exemplary classifiers include: Multiple Instance Learning (MIL) based methods, one or more neural networks which may include an individual neural network and/or an architecture of multiple neural networks (e.g., convolutional neural network (CNN), fully connected neural network), deep learning based methods, support vector machine (SVM), logistic regression, k-nearest neighbor, and decision trees.

A process of training the classifier is described with reference to FIG. 2.

At 104, one or more images are captured, where each image includes one or more weeds of one or more species. Images without weeds may be automatically discarded and/or ignored by the classifier.

The images may be captured by a stationary sensor(s), for example, an array of surveillance cameras that monitor a field. The images may be captured by a mobile sensor(s), for example, imaging sensor(s) attached to land and/or aerial machineries that navigate over the field, for example, a tractor driving over the land and/or a drone flying over the field.

The images depict the weed(s) at various growth states. The weed(s) captured in the image(s) may be presently at the target growth state. Alternatively or additionally, the at least one image captured by the imaging sensor depicts the weed(s) species of interest at a growth stage prior the start of flowering. In such a case, when the target growth state is after the start of flowering, the future time interval when the target growth state is reached is predicted based on the image depicting the weed prior to the start of flowering.

At 105, the image(s) may be pre-processed for extraction of weed(s) from the image(s). The image(s) may include background and/or other objects in addition to the weed(s), for example, other plants, crops, rocks, and/or earth.

The images may be pre-processed by executing segmentation code for segmenting the weed(s), and feeding the segmented weed(s) to the classifier. The segmentation code may be implemented based on, for example, matching weed(s) within the image to a set of weed templates, another classifier (e.g., neural network) that is trained to segment weed(s) from images with background and/or other objects, and/or code that segments weed(s) based on a set-of rules (e.g., edge detection, thresholding methods, color detection, shape detection).

Alternatively, the whole image or portions thereof (i.e., with background and/or other objects) is processed by the classifier.

At 106, each image may be time stamped with an indication of the time and/or date at which it was taken, for example, stored as metadata and/or as a tag. The current time may be obtained, for example, by accessing a server that provides the current real time in response to a query.

Alternatively or additionally, the image(s) may be associated with an indication of the geographical location from which the respective image was taken and/or the geographical location depicted within the scene captured in the image (e.g., as metadata, a tag, a set of coordinates). The geographical location may be obtained from a geographical location sensor associated with the imaging sensor and/or the machinery on which the imaging sensor is installed, and/or from a dataset storing known locations. For example, the location of the field being images has been determined once and stored for future reference.

Alternatively or additionally, the image(s) may be associated with the supplemental data profile, as described herein. The parameters of the supplemental data profile may be obtained, for example, from a server storing data, and/or outputted by sensors (e.g., temperature sensors, humidity sensor).

At 108, the image(s) are fed into the classifier. The date and/or geographical location and/or supplemental data may be fed into the classifier in association with the image(s).

At 110, the classifier(s) compute an indication of likelihood of the weed(s) depicted in the image(s) being at a target growth state suitable for artificial pollination of flowers of the weed species of interest at a certain time interval.

The target growth state suitable for artificial pollination of flowers of the weed species of interest may include flowering of the weed species of interest, and/or other growth stages described herein. It is noted that different target growth states may be suitable for artificial pollination of different weeds.

The certain time interval may be a future time interval relative to the time at which the image(s) is captured, for example, 1 day in the future, 3 days, 1 week, 2 weeks, 1 month, or 2 months, or other values. Alternatively or additionally, the certain time interval denotes a current time, indicating that the weed is presently in the target growth state suitable for artificial pollination.

It is noted that different weeds, of the same or different species, in the same or different images, may be associated with different target growth states that are reached at different time intervals.

Optionally, the classifier(s) computes an indication of the number and/or density of weeds appearing with the image(s). Alternatively, the number and/or density of weeds appearing with the image(s) is computed by other code, for example, the segmentation method that segments weeds from the images, and/or the according to the code that divides the image into sub-images and feeds each sub-image into the classifier, by counting the number of results outputted by the classifier for each sub-image.

Optionally, the classifier(s) computes a classification indication that the weed depicted in the image is a female or a male. The female or male types of the weed may be associated with different target growth states suitable for artificial pollination thereof. Different instructions for pollination may be generated according to whether the weed is female or male.

The indication may represent an absolute value. For example, the weed is currently in the target growth state suitable for artificial pollination, the weeds in the image will be in the target growth state suitable for artificial pollination in 2 weeks. Alternatively or additionally, the indication may represent a probability values. For example, 80% probability that the weed is currently in the target growth state suitable for artificial pollination, 70% probability that the weeds in the image will be in the target growth state suitable for artificial pollination in 2 weeks.

At 112, instructions for execution by a pollination controller of a pollinator device are generated according to the indication and/or the certain time interval outputted by the classifier. The instructions are for artificially pollinating flowers of the weed(s) species of interest with pollen that reduces fitness of the weed(s) species of interest.

The instructions may be automatically generated based on code executed by a processor(s), for example, as binary code, as a script, as human readable text, as source code, as compiled code, and/or as function calls. Alternatively or additionally, the instructions are manually generated by a user presented with the output of the classifier (e.g., the user programs the pollination controller and/or presses buttons to activate the pollination controller).

The instruction may be generated according to the male or female classification.

The instructions may be generated according to the geographic location of weed(s) and/or the supplemental data profile. For example, taking into account the temperature, humidity, altitude, wind speed, wind direction, dispersion patterns, hardware of the pollinator, and/or type of artificial pollination. The instructions may be dynamically generated in real time according to real time updates of the supplemental data, for example, dynamically adjusted according to changing wind speed and/or wind direction.

Alternatively or additionally, the instructions may be dynamically generated in real time according to a real time location of the pollination device (e.g., installed on machinery such as a vehicle) outputted by a geographical location sensor that senses the location of the pollination device (and/or location of the machinery). For example, the density and/or amount of pollen is dynamically adjusted for different locations based on the number of weeds determined at each location.

Alternatively or additionally, the instructions are generated in real time according to environmental condition parameter(s) (e.g., humidity, wind speed, temperature, wind direction, and level of pollen in the air) outputted by environmental condition sensor(s) that senses the environmental condition in proximity to the weed(s) species of interest. The instructions may be generated according to a predicted dispersion pattern of the applied pollen according to the environmental condition parameter(s).

It is noted that different sub-instructions may be generated for different weeds and/or different locations of the field having weeds of the same or different species, according to different target growth states and/or according to different time intervals.

The instructions may be computed by the classifier, for example, when the classifier is trained to compute such instructions according to a training dataset storing training instructions. Alternatively or additionally, the instructions are computed by other code, for example, based on a defined algorithm, function, and/or machine learning based methods.

At 114, the generated instructions for artificially pollinating flowers of the weed(s) species of interest with pollen that reduces fitness thereof are executed by the pollinator controller and/or the pollinator device. For example, the weeds are sprayed with pollen according to the instructions.

At 116 one or more acts described with reference to blocks 104-112 are iterated. Exemplary implementations are now described, based on the iterations.

In a first implementation, the image sensor(s) is coupled to machinery (e.g., vehicle) navigating over the field and/or the image sensor(s) is coupled to a stationary fixture (e.g., pole). The instructions for execution include code instruction for automated execution by the pollination controller of the pollinator device coupled to the machinery and/or stationary located. The image(s) are iteratively acquired by the imaging sensor(s), and the pollination controller of the pollinator device iteratively executes the code instructions generated in response to the acquired images. The iterations are performed as the machinery navigates over the field for real-time pollination of identified weed species of interest. In another example, the pollinator device is stationary, and the pollination controller of the pollinator device iteratively executes the code instructions generated in response to the acquired images. The iterations are performed in real time as the machinery navigates over the field for real-time pollination of identified weed species of interest. In yet another example, both the sensor and the pollinator device are stationary, for real time monitoring and pollination.

In a second implementation, the instructions for pollination are created according to multiple images, where each image is associated with a different geographical location. For example, different cameras are stationary positioned at different locations of the field to monitor different locations. In another example, the sensor is installed on a machinery (e.g., vehicle) that navigates over the field. In such case, the same sensor captures images of different parts of the field as the machinery navigates over the field. The instructions for pollination may be generated as sub-sets of instructions for administering pollen to each weed(s) species of interest located at respective geographical locations of a field. Each of the sub-sets of instructions is selected for execution by the pollination controller of the pollinator device according to a real-time geographic location of the machinery navigating over the field. Is it noted that the sub-sets of instructions may be created at approximately the same time such as when multiple cameras image different parts of the field at approximately the same time. Alternatively or additionally, the sub-sets of instructions may be sequentially created as the machinery navigates over the field and the image sensor(s) on the machinery sequentially capture images of different locations of the field.

In a third implementation, the image sensor(s) is coupled to a stationary fixture (e.g., poles) that monitor the field. The pollination controller and/or the pollinator device are coupled to machinery (e.g., vehicle). The image(s) are iteratively acquired by the imaging sensor(s), and the pollination controller of the pollinator device iteratively executes the code instructions generated in response to the acquired images. The iterations are performed as the machinery navigate over the field for real-time pollination of identified weed species of interest.

In a fourth implementation, the image sensor(s) is captured during a first time interval. The instructions are executed by the pollinator device and/or pollinator controller at a second time interval. The second time interval is spaced apart in time after the first time interval. The second time interval is according to the certain time interval computed by the classifier. For example, images are acquired on day 1, with a prediction that the weeds will reach the state suitable for artificial pollination on day 10. The pollinator artificially pollinates the weeds on day 10 according to the generated instructions. The image sensor(s) may be coupled (e.g., installed on) a first machinery (type) navigating over the field during the first time interval, and the pollination controller may be coupled to a second machinery (type) navigating over the field during the second time interval. The first and second machinery may be different types, for example, a drone may fly over the field capturing image on day 1, and the tractor with pollinator device may drive over the field to pollinate the weeds on day 10 according to the generated instructions.

In another example, the image sensor(s) may be coupled (e.g., installed on) a stationary fixture (e.g., pole) that monitors the field during the first time interval, and the pollination controller may be coupled to a stationary device that applies the artificial pollination during the second time interval.

In another example, the same machinery with pollinator device may be repeatedly dispatched to pollinate different weeds and/or different species of weeds that reach the target growth state at different times.

Referring now to FIG. 2, at 202, multiple images are provided. The images may be acquired by different imaging sensor(s), or by the same imaging sensor(s). Each image includes one or more weeds or one or more species of interest, depending on the type of classified to be trained.

At 203, the image(s) are optionally pre-processed for extraction of weed(s) from the image(s). The image(s) may include background and/or other objects in addition to the weed(s), for example, other plants, crops, rocks, and/or earth.

The images may be pre-processed by executing segmentation code for segmenting the weed(s), and training the classifier(s) based on the segmented weed(s). The segmentation code may be implemented based on, for example, matching weed(s) within the image to a set of weed templates, another classifier (e.g., neural network) that is trained to segment weed(s) from images with background and/or other objects, and/or code that segments weed(s) based on a set-of rules (e.g., edge detection, thresholding methods, color detection, shape detection).

Alternatively, the classifier is trained based on the whole image(s) or portions thereof (i.e., with background and/or other objects).

At 204, each image may be associated with a time stamp indicating the time and/or date when the respective image was captured, a geographic location indication the location depicted within the image (e.g., outputted by a location sensor(s) as described herein), and/or supplemental data profile (as described herein).

At 206, an indication of a time interval of when the respective at weed(s) species of interest reach a target growth state suitable for artificial pollination of flowers thereof relative to the time of capture of the respective image, is provided. The indication may be manually defined by a user, for example, a botanist expert specializing in weeds. Alternatively or additionally, the indication may be automatically computed by code, for example, code that analyzes images obtained at a future time to identify the same weeds of the original images that reached the target growth state, and assigning the time interval the original image based on the time elapsed between the original image and the image depicting the weed reaching the target growth state.

At 208, one or more training datasets are created based on the image and associated data. The training datasets may be defined according to different desired classifiers, as described herein.

At 210, one or more classifiers are trained according to the one or more training dataset.

At 212, the one or more classifiers are provided, for example stored on the computing device to provide services to one or more pollinator controllers and/or pollinator devices and/or client terminals, as described herein.

At 214, one or more acts described with reference to blocks 202-210 may be iterated, for example, for updating the classifier(s).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

In addition, any priority document(s) of this application is/are hereby incorporated herein by reference in its/their entirety.

What is claimed is:

1. A system for reducing fitness of at least one weed species of interest, comprising:
    a non-transitory memory having stored thereon a code for execution by at least one hardware processor, the code comprising:
        code for inputting into at least one classifier, at least one image captured by at least one imaging sensor, the at least one image depicting at least one weed species of interest;
        code for computing by the at least one classifier, an indication of likelihood of the at least one weed being at a flowering state suitable for being artificially pollinated by artificial pollination of flowers of the at least one weed species of interest at a certain time interval, wherein the at least one classifier is trained on a training dataset comprising a plurality of images of respective at least one weed species of interest captured by the at least one imaging sensor and associated indication of a time interval of when the respective at least one weed species of interest is at the target flowering state suitable for being artificially pollinated by artificial pollination of flowers thereof relative to the time of capture of the respective image; and
        code for generating according to the indication of likelihood and the certain time interval, instructions for execution by pollination controller of a pollinator device for artificially pollinating flowers of the at least one weed species of interest with pollen that reduces fitness of the at least one weed species of interest.

2. The system of claim 1, wherein the certain time interval is a future time interval relative to the time at which the at least one image is captured.

3. The system of claim 1, wherein the certain time interval denotes a current time.

4. The system of claim 1, wherein the at least one image captured by at least one imaging sensor depicts the at least one weed species of interest at a flowering stage prior the start of flowering.

5. The system of claim 1, further comprising code for execution of the generated instructions for artificially pollinating flowers of the at least one weed species of interest with pollen that reduces fitness of the at least one weed species of interest.

6. The system of claim 1, wherein the instructions for execution by pollination controller are computed by at least one classifier according to the training dataset that further includes, in association with each of the plurality of images, respective instructions for execution by pollination controller of a pollinator device for artificially pollinating flowers of the at least one weed species of interest with pollen that reduces fitness of the at least one weed species of interest.

7. The system of claim 1, wherein the at least one image sensor is coupled to a first machinery navigating over the field, and the instructions for execution comprise code instruction for automated execution by the pollination controller of the pollinator device coupled to a second machinery navigating over the field, wherein the at least one image is iteratively acquired by the at least one sensor and the pollination controller of the pollinator device iteratively executes the code instructions as the first machinery and the second machinery navigate over the field for real-time pollination of identified at least one weed species of interest.

8. The system of claim 1, wherein the at least one image sensor is captured during a first time interval, and the instructions for execution comprise code instruction for automated execution by the pollination controller of the pollinator are executed at a second time interval spaced apart in time after the first time interval, wherein the second time interval is according to the certain time interval computed by the classifier.

9. The system of claim 1, wherein the at least one classifier further computes for the at least one image, a classification indication of at least one of a female of the at least one weed species of interest, or a male of the at least one weed species of interest, wherein the instructions for artificially pollinating flowers are generating according to the classification indication, and wherein images of the training set respectively include a classification indication of a female of the at least one weed species of interest.

10. The system of claim 1, wherein the at least one image is further associated with a tag storing a geographical location indication of the at least one weed species of interest captured within the at least one image, the geographic location outputted by at least one geographic positioning sensor, and wherein the instructions for pollination of the at least one weed species of interest are generated according to the geographic location of the at least one weed, wherein the instructions for pollination are created according to a plurality of images, each image associated with a different geographical location, the instructions for pollination comprise sub-sets of instructions for administering pollen to each at least one weed species of interest located at respective geographical locations of a field, wherein each of the sub-sets of instructions is selected for execution by the pollination controller of the pollinator device according to a real-time geographic location of a machinery navigating over the field.

11. The system of claim 1, wherein the instructions are generated in real time according to a real time location of the pollination device outputted by a geographical location sensor that senses the location of the pollination device.

12. The system of claim 1, wherein the instructions are generated in real time according to at least one environmental condition parameter outputted by at least one environmental condition sensor that senses the environmental condition in proximity to the at least one weed species of interest, wherein the instructions are generated according to a predicted dispersion pattern of the applied pollen according to the at least one environmental condition parameter.

13. The system of claim 1, wherein the at least one imaging sensor is selected from the group consisting of: a reflectance sensor that captures light applied by a light source reflected from the at least one weed species of interest, a spectral image sensor, multispectral image sensor, hyperspectral image sensor, and a visible light sensor.

14. The system of claim 1, wherein the pollinator device comprises a sprayer located at a predefined height above the ground, and above crops growing in the field where the at least one weed species of interest is growing.

15. The system of claim 1, wherein the pollinator device is coupled to an aerial based machinery selected from the group consisting of: an unmanned aerial vehicle (UAV), a remote-piloted vehicle (RPV), a drone, a specialized robot, a robot bee, a robobee, and a robo-bee.

16. The system of claim 1, wherein the pollinator device comprises a mechanism to attract bees, and couple the pollen to the bees for administration to the flower of the at least one weed species of interest.

17. The system of claim 1, wherein the instructions are generated according to a supplemental data profile including multiple supplemental data parameters indicative of the environment of the weed and/or details of the pollination to be applied and/or hardware of the pollinator device.

18. A system for training at least one classifier for reducing fitness of at least one weed species of interest, comprising:

a non-transitory memory having stored thereon a code for execution by at least one hardware processor, the code comprising:

code for accessing a training dataset comprising a plurality of images of respective at least one weed species of interest captured by at least one imaging sensor and associated indication of a time interval of when the respective at least one weed species of interest is at a target flowering state suitable for being artificially pollinated by artificial pollination of flowers thereof relative to the time of capture of the respective image; and code for training at least one classifier according to the training dataset, for computing an indicative of likelihood of a target at least one weed being at a target flowering state suitable for being artificially pollinated by artificial pollination of flowers of the at least one weed species of interest at a certain time interval according to at least one target image captured by at least one imaging sensor.

19. A method of reducing fitness of at least one weed species of interest, comprising:

inputting into at least one classifier, at least one image captured by at least one imaging sensor, the at least one image depicting at least one weed species of interest;

computing by the at least one classifier, an indication of likelihood of the at least one weed being at a target flowering state suitable for being artificially pollinated by artificial pollination of flowers of the at least one weed species of interest at a certain time interval, wherein the at least one classifier is trained on a training dataset comprising a plurality of images of respective at least one weed species of interest captured by the at least one imaging sensor and associated indication of a time interval of when the respective at least one weed species of interest is at the target flowering state suitable for being artificially pollinated by artificial pollination of flowers thereof relative to the time of capture of the respective image; and generating according to the indication of likelihood and the certain time interval, instructions for execution by pollination controller of a pollinator device for artificially pollinating flowers of the at least one weed species of interest with pollen that reduces fitness of the at least one weed species of interest.

* * * * *